(12) United States Patent
Degany et al.

(10) Patent No.: US 6,193,669 B1
(45) Date of Patent: Feb. 27, 2001

(54) SYSTEM AND METHOD FOR DETECTING, LOCALIZING, AND CHARACTERIZING OCCLUSIONS, STENT POSITIONING, DISSECTIONS AND ANEURYSMS IN A VESSEL

(75) Inventors: Elhanan Degany; Simon Henri Noskowicz, both of Kfar Saba; Evgeny Shalman; Alexander Tyomkin, both of Tel-Aviv; Chen Barak, Shoam, all of (IL)

(73) Assignee: Florence Medical Ltd., Kfar Saba (IL)

( * ) Notice: Subject to any disclaimer, the term of this patent is extended or adjusted under 35 U.S.C. 154(b) by 0 days.

(21) Appl. No.: 09/210,002

(22) Filed: Dec. 11, 1998

(51) Int. Cl.[7] ....................................... A61B 5/02
(52) U.S. Cl. ...................... 600/486; 600/500; 600/504; 600/561
(58) Field of Search .................... 600/485–486, 600/500, 504–505, 454, 481, 561

(56) References Cited

U.S. PATENT DOCUMENTS 5,343,867 * 9/1994 Shankar ........................... 600/481
5,690,115 * 11/1997 Feldman et al. ................. 600/454

* cited by examiner

Primary Examiner—Cary O'Connor
Assistant Examiner—Ryan Carter
(74) Attorney, Agent, or Firm—Eitan, Pearl, Latzer & Cohen-Zedek

(57) ABSTRACT

This invention relates to a method and devices for detection, localization and characterization of occlusions, aneurysms, dissections stent position, dissections stent mal-position, wall characteristics and vascular bed. The invention is based on introducing an artificial pressure or flow excitation signal (a single signal or more) into the blood vessel (or in other tubular flowing fluid conduits), measurement and analysis of the pressure and or flow. The invention discloses a method and devices for detection and characterization of partial or total occlusion or aneurysm in blood vessels or in other tubular flowing fluid conduits within a body, such as urine flow in the urethra.

71 Claims, 35 Drawing Sheets

SYSTEM AND METHOD FOR DETECTING, LOCALIZING, AND CHARACTERIZING OCCLUSIONS, STENT POSITIONING, DISSECTIONS AND ANEURYSMS IN A VESSEL

FIELD OF THE INVENTION

This invention relates to the field of medical interventional diagnostic devices. In particular, this invention provides a system and method for the detection, localization, and characterization of occlusions and aneurysms in blood or other body vessels and to the evaluation of clinical treatment success (e.g. tracking sufficient opening of the occlusion or malpositioning of a stent). Also, this invention provides a method and system for vessel wall characterization and diagnosis of the vascular bed.

BACKGROUND OF THE INVENTION

Vascular diseases are often manifested by reduced blood flow due to atherosclerotic occlusion of vessels. For example, occlusion of the coronary arteries supplying blood to the heart muscle is a major cause of heart disease. Invasive procedures for relieving arterial blockage such as bypass surgery and balloon dilatation with a catheter are currently performed relying on estimates of the occlusion characteristics and the blood flow through the occluded artery. These estimates are based on measurements of occlusion size and/or blood flow or blood pressure before and after the stenosis. Unfortunately, current methods of occlusion size and blood flow measurement have low resolution, are inaccurate, are time consuming, require expertise in the interpretation of the results and are expensive. Thus, decisions on whether or not to use any of the blockage relieving methods and which of the methods should be used are often based on partial information. The evaluation of therapeutic success is also problematic, where both occlusion opening and stent position must be evaluated.

Typically, the physician first selects the appropriate treatment method from among medication therapy, transcatheter cardiovascular therapeutics (TCT), coronary artery bypass grafting (CABG), or non-treatment. Atherosclerotic lesions may have different characteristics. Some lesions exhibit a variable degree of calcification while others have a fatty or thrombotic nature. Lesion characteristics together with vessel condition distal to the lesion and the vascular bed (VB) condition are the major factors for determining the therapeutic procedure needed. Recently, increasing numbers of patients are directed toward TCT. TCT starts with an interventional diagnosis procedure (most commonly used in angiography), followed by the treatment of the patient with medication therapy, CABG or continuation of the TCT procedure with adequate interventional treatment. TCT final stage include diagnosis tools, for the evaluation of treatment success.

Numerous methods are currently available for treating various lesion types. Some of these methods are given herein below, sequenced from "softer" to "heavier", relating to their ability to open calcified lesions; percutaneous transluminal angioplasty (PTCA), "Cutting balloon" angioplasty, directional coronary atherectomy (DCA), rotational coronary atherectomy (RCA), Ultrasonic breaking catheter angioplasty, transluminal extraction catheter (TEC) atherectomy, Rotablator atherectomy, and excimer laser angioplasty (ELCA). Often, stents are placed within the lesion so as to prevent re-closure of the vessel (also known as recoil). If the stent is malpositioned, it disrupts the flow and may initiate restenosis.

Lesion characteristics, together with vessel condition proximal and distal to the lesion and vascular bed condition are used to determine the medically and economically optimal treatment method or combination of methods of choice. The main geometrical parameter of the lesion is stenosis severity As/Ao. Here As is the minimal open cross-sectional area of the stenosis and Ao is the nominal cross-sectional area of the unobstructed vessel. The second parameter is the stenosis length. Another clinically important lesion characteristic is the lesion calcification level. A non-calcified arterial wall or lesion is usually a non-chronic, fat based plaque that may be treated by medication therapy, or by the softer, less expensive, PTCA method. Heavily calcified lesion typically requires harder methods, such as ELCA. The calcification level influences the decision whether to use a dilatation balloon prior to stenting. For example, in cases of very soft lesions, the physician may elect not to use a dilatation balloon prior to stenting. In cases where the degree of calcification dictate the use of such a balloon, the vessel wall calcification level influences the optimal inflation pressure of the dilatation balloon. Chapter 12 entitled "CALCIFIED LESIONS" of the book "The New Manual of Interventional Cardiology" (Eds. Mark Freed, Cindy Grines and Robert D. Safian, Physicians' Press, Birmingham, Mich., 1996, pp. 251–261), discusses various methods for the assessment of the degree of vessel wall calcification and their importance in selecting a treatment method.

Decisions about post dilatation processes such as stent deployment for preventing wall recoil and restenosis, or radiation exposure for preventing restenosis caused by cell proliferation, are also influenced by vessel wall and lesion characteristics. Unfortunately, while lesion geometry is evaluated by angiography, qualitative coronary angiography (QCA), or by intravascular ultrasound (IVUS), accurate information regarding the vessel wall structure and composition and the degree of calcification of the lesion and of the vessel wall sections neighboring the lesion is frequently unavailable due to the expenses involved in obtaining this information. Angiography has been the main diagnostic tool in the cath lab. The physician interprets angiographical images in the following sequence: identification and location of the severe lesions, evaluation of the occlusion level (in diameter percentage of the occluded portion), qualitative estimation of the perfusion according to "thrombolysis in myocardial infarction" (TIMI) grades, determined according to the contrast material appearance. TIMI grades 0, 1, 2, 3 represent no perfusion, minimal perfusion, partial perfusion and complete perfusion, respectively.

Among the more sophisticated diagnostic tools are qualitative coronary angiography (QCA), intravascular ultrasound (IVUS), intravascular Doppler velocity sensor (IDVS) and intravascular pressure sensor (IPS). QCA calculates geometrical properties from angiographic images, in image zones that are chosen by the physician. IVUS provides accurate geometrical data regarding cross section and accurate information regarding the vessel wall structure and composition. Physiological parameters have been introduced in order to help the clinician to elect the appropriate clinical solution. IDVS provides velocity measurements, enabling discriminating various degrees of occlusion according to coronary flow reserve (CFR) criteria. IDVS suffers from inaccuracy problems resulting from positioning error within the vessel.

IPS provides pressure measurements enabling discriminating various degrees of occlusion according to the FFR (fractional flow reserve) criteria and according to the pressure drop across the stenosis. While measuring the pressure based parameters, the transducer should cross the stenosis and measure pressure downstream of the stenosis. The need to cross the stenosis prevents the use of this parameters for purely diagnostic purposes, since stenosis crossing is considered of high risk and therefore, unjustified for diagnostic purposes.

Angiography and the sophisticated techniques discussed above may be employed prior to and after therapeutic procedure (the last for the evaluation of the results and decision about correcting actions). unfortunately, the above discussed sophisticated methods are rarely used due to their high price, operation complexity and the prevailing feeling among physicians that while they provide more accurate information, this information usually does not contribute to clinical decisions.

Pressure, flow and geometry are three variables often measured in the cardiovascular system. Recent progress in invasive probe miniaturization, improvements of the frequency response of probe sensors and computerized processing have opened a whole new range of intravascular pressure and flow measurements and analysis that have been previously impossible to perform. A method for determination of the reflection sites in the arterial system was suggested by Pythoud, F. Stergiopulos, N. Westerhof, N. and Meister, J. J. in "Method for determining distributions of reflection sites in the arterial system" in Am. J. Physiol 271 (1996). They studied reflections of pressure and flow waves generated by the beating heart, in the arterial tree using simultaneous pressure and flow measurements. The low (up to 10 Hz) bandwidth of the pressure and flow signals prevent accurate determination of the distance to reflection site by these authors. Correct determination of reflection source location requires accurate estimation of the pressure wave velocity (PWV) in the vessels under consideration and under the specific pressure signal, in contrast with literature data that is based on healthy arteries under beating heart pulses. All known methods for PWV measurement, used two, three or more simultaneous measurements, which prove impractical considering clinically available tools and methods. Further, various attempts have been done to analyze pressure and flow wave changes caused by occluded sites. Harmonic distortions, changes in pressure wave velocity phase velocity, wave attenuation, and additional reflection sites within the arterial tree prevent successful interpretation and implementation within clinical methods or tools.

SUMMARY OF THE INVENTION

The invention discloses a method and devices for detection, localization and characterization of occlusions, aneurysms, wall characteristics and vascular bed by introducing an artificial pressure or flow excitation signal (a single signal or multiple signals) into the blood vessel (or in any other tubular flowing fluid conduits), measurement and analysis of the pressure and or flow. The invention provides a method and devices for detection and characterization of partial or total occlusion or aneurysm in blood vessels or in other tubular flowing fluid conduits within a body, such as urine flow in the urethra.

This invention provides a method and devices may also serve for evaluating the success of medical treatment. For example tracking sufficient opening of the occlusion or malpositioning of a stent. It may also serve for the characterization of vascular bed, downstream the vessel.

The present invention includes also a method for further analysis of the response to the excitation signal yielding a quantitative determination of elastic properties of blood vessel walls for characterizing, inter alia, the distensibility and the compliance of lesioned and non-lesioned parts of blood vessels. The derived elastic properties may be further used to determine the degree of calcification of lesioned and non-lesioned parts of blood vessels.

This invention provides an apparatus for detecting, locating and characterizing changes in a tubular conduit system within a living body for transferring fluids, said apparatus comprising: a signal generator configured to transmit into said tubular conduit a probe signal that changes in response to encountering changes in said tubular conduit system; a signal sensor operative to receive said probe signal following transmission into said tubular conduit system; a processor unit operatively connected to said signal sensor; a program for controlling the processor unit; said processor unit operative with said program to receive said probe signal following transmission through said tubular conduit system: identify changes in said probe signal; detect characteristics of said tubular conduit system, said characteristics of said tubular conduit system being derived from changes in said probe signal; and recognize and assign a label said characteristic of said tubular conduit said system.

This invention provides a processor apparatus for detecting, locating and characterizing changes in a tubular conduit system within a living body for transferring fluids for use with a signal generator configured to transmit into said tubular conduit a probe signal that changes in response to encountering changes in said tubular conduit system and a signal sensor operative to receive said probe signal following transmission into said tubular conduit system, said processor apparatus comprising: a processor unit operatively connected to said signal sensor; a program for controlling the processor unit; said processor unit operative with said program to receive said probe signal following transmission through said tubular conduit system: identify changes in said probe signal; detect characteristics of said tubular conduit system, said characteristics of said tubular conduit system being derived from changes in said probe signal; recognize and assign a label said characteristic of said tubular conduit said system; and ascertain and assign a value corresponding to the location and size of said characteristic of said tubular conduit.

This invention provides a method for using a computer to detect, locate and characterize changes in a tubular conduit system within a living body for transferring fluids wherein said computer is operatively connected to a signal generator configured to transmit into said tubular conduit a probe signal that changes in response to encountering changes in said tubular conduit system and a signal sensor operative to receive said probe signal following transmission into said tubular conduit system, said method comprising the steps of: receiving said probe signal following transmission through said tubular conduit system: identify changes in said probe signal; detecting characteristics of said tubular conduit system, said characteristics of said tubular conduit system being derived from changes in said probe signal; and recognizing and assigning a label said characteristic of said tubular conduit said system.

Lastly, the present invention includes also a method for further analysis of the response to the excitation signal yielding a quantitative determination of elastic properties of blood vessel walls for characterizing, inter alia, the distensibility and the compliance of lesioned and non-lesioned parts of blood vessels. The derived elastic properties may be further used to determine the degree of calcification of lesioned and non-lesioned parts of blood vessels.

BRIEF DESCRIPTION OF THE DRAWINGS

The present invention will be understood and appreciated more fully from the following detailed description taken in conjunction with the appended drawings in which like components are designated by like reference numerals:

FIG. 29(a) is a schematic of an impulse generator. The generator could generate pulses with different width from 2 micro sec. To 1.6 sec. And with period (distance between pulses) from 2 micro sec. To 2.3 sec. For better adjustment the width and the period are divided to 6 regions and related by 4 separate regulators, 2 for period and 3 for the pulse width. The electric pulse generator work from power supply of 9 V. The standard timer microchip 556. FIG. 29(b) is a schematic showing electric pulse generator connected to external equipment which will transfer the electric impulse to an impulse of flow/pressure.

Figure 1:
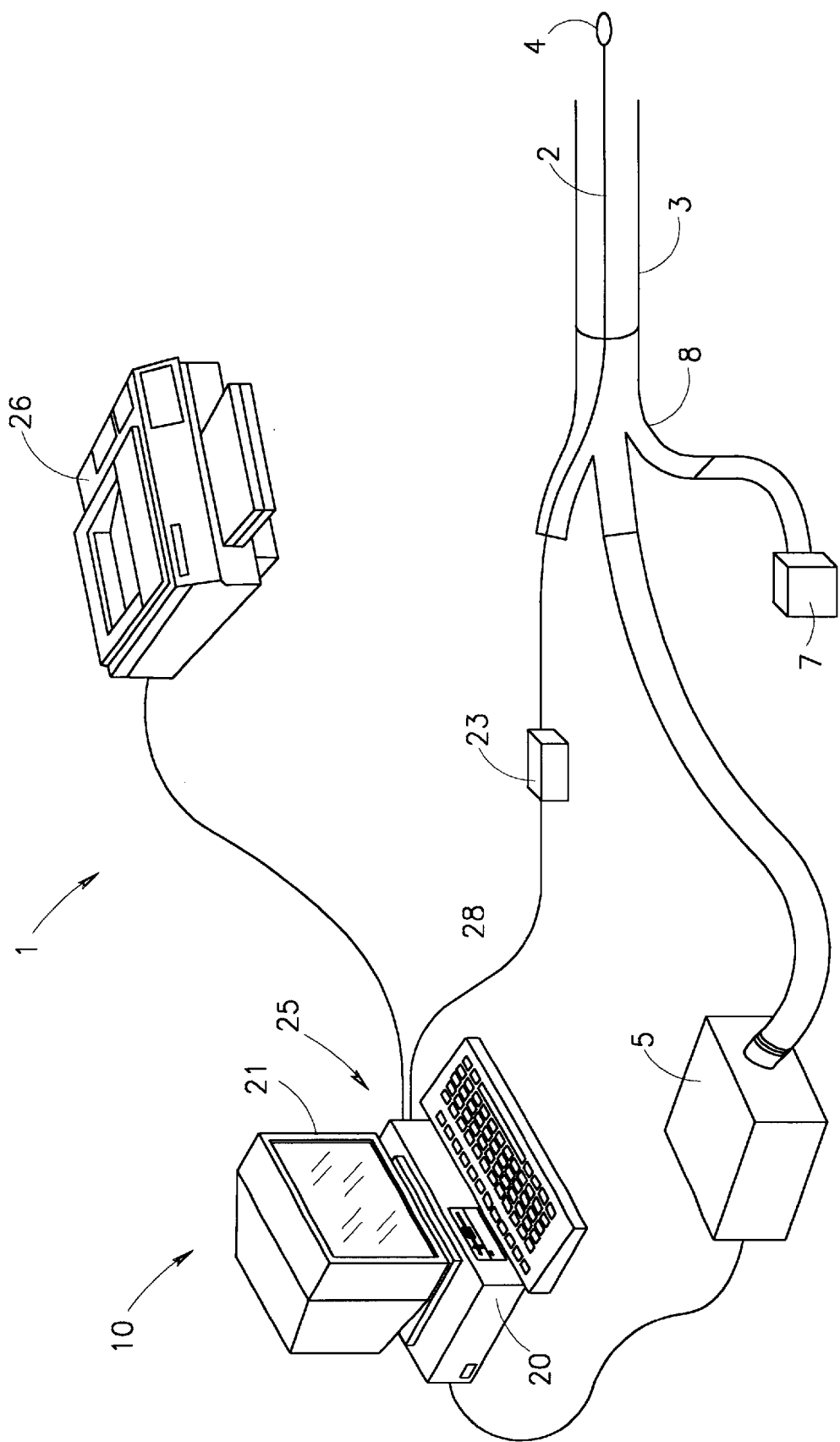
FIG. 1 is a schematic view of a clinical system used for characterizing lesions, aneurysm or vascular bed in blood vessels, constructed and operative in accordance with a preferred embodiment of this invention.

DETAILED DESCRIPTION OF THE INVENTION the form of the pressure and flow wave changes at different locations along the arterial system. The most obvious reason is reflection of the advancing pulse originating by the heart beat from occlusions. Analysis of the pressure and or flow waveform as demonstrated herein identifies and quantifies abnormalities within arteries, mainly occlusions. Pressure wave velocity has its own clinical value as a measure of distensibility or compliance. Significant changes are observed in the hemodynamic characteristics of blood vessels with aging and/or disease-state such as hypertension and atherosclerosis. The nature of heart beat rather than low bandwidth and its heart generated pulse variance complicates PWV calculations. The variability of pulse sources beating heart imposes inherent variance between measurements taken either in different patients and even between measurements taken in the same patient but at different times or even the same patient, same time different artery. Basically, the large arteries dilate and stiffen, the collagen/elastin ratio increases, thus reducing the vessel distensibility. For example, the elastic modulus of the human aorta, more than doubles between the age of 20 and 60 years. The diameter of the human ascending aorta increases by 9% per decade, and the aorta wall thickens to a larger extent, raising the ratio of the vessel wall thickness to the vessel's radius. These processes result in an increased pressure wave velocity (PWV) within the vessel. Calcification of the vessel wall in particular regions causes significant increase in PWV in the calcified region.

Regions where PWV increases and decreases along the blood vessel as demonstrated herein mark the calcified zone boundaries, and the increase in the PWV above a reference value are used for evaluating the compliance and the calcification level. The determined value of the PWV are compared to the average PWV value, predetermined statistically for the same blood vessel in a specific age and gender group to which the current patient belongs by calculating and reporting their ratio. Additionally, the PWV value determined within the lesion region may be compared to the PWV value(s) determined within one or more non-lesion regions of the same vessel which serve as an internal reference value, by calculating and reporting the ratio of the above PWV values. These PWV measurements and the reported PWV ratio disclosed hereinabove, are useful in the detection of otherwise "angiographically occult" diseased vessel regions.

This invention provides an apparatus for detecting, locating and characterizing changes in a tubular conduit system within a living body for transferring fluids, said apparatus comprising: a signal generator configured to transmit into said tubular conduit a probe signal that changes in response to encountering changes in said tubular conduit system; a signal sensor operative to receive said probe signal following transmission into said tubular conduit system; a processor unit operatively connected to said signal sensor; a program for controlling the processor unit; said processor unit operative with said program to receive said probe signal following transmission through said tubular conduit system: identify changes in said probe signal; detect characteristics of said tubular conduit system, said characteristics of said tubular conduit system being derived from changes in said probe signal; and recognize and assign a label said characteristic of said tubular conduit said system.

In one embodiment the pressure signal originates from catheterization laboratory injection system. The signal may be either one of the internally generated waveforms or excited electronically from a separate signal generator either a stand alone unit or integrated within the system computer, otherwise used for data acquisition and analysis. In another embodiment the pressure signal may originate from an impact mechanism system, e.g. a spring loaded or electronically activated mechanical impact system, applying pressure on either the catheter or on a container attached to it. In one embodiment the processor unit is operative to select a method from a plurality of methods to identify changes in said probe signal and therefrom detect changes in said tubular conduit system. For example, the processor unit is operative to detect aneurysms, stenosis, and/or arterial occlusions.

The method is based on introducing an artificial pressure signal into the blood vessel. In one embodiment the pressure signal originates from a pressure signal generator (PSG). For example, a PSG of the type suitable for this purpose is a "blood pressure systems calibrator" model 601A, commercially available from Bio-Tek Instruments Inc., Highland Park, Box 998, Winooski, Vt.-05404-0998, U.S.A. Catheterization laboratory injection systems are known to those skilled in the art. For example, a system of the type suitable for this purpose is a "Mark V Plus Injection System" from Medrad, inc. 271 Kappa Drive, Pittsburgh, Pa. 15238-2870 U.S.A. Other examples include but are not limited to the following: a pressure signal generated within the catheter or in its distal tip (e.g. piezoelectrically or by another form of energy burst introduction e.g. AcolysisSystem, ultrasound thrombolysis selective lysis of fibrin, by Angiosonics Inc., NC, U.S.A.); is by the movement of an hydrodynamic surface, activated either manually or by a special mechanism (e.g. catheter used for removing malpositioned or embolized stents, for example Amplatz Goose Neck Snare GN 500 and Microsnare SK200 from Microvena corporation, Minnesota USA and catheters which prevent plaque debris from moving downstream); a pressure signal caused by an external controlled pressure applied on an organ, transmitted into a pressure signal within the vessel; a pressure signal caused by a non-invasive energy transmission into the vessel (e.g. ultrasound) in which the artificial pressure/flow signal may be either controlled or measured (within the catheter or the vessel).

In one embodiment the signal generator is a pressure signal generator. As contemplated herein the signal generator is a pressure sensor. In another embodiment the signal generator is a flow signal generator. As contemplated herein the signal generator is a pressure sensor.

Figure 29A:
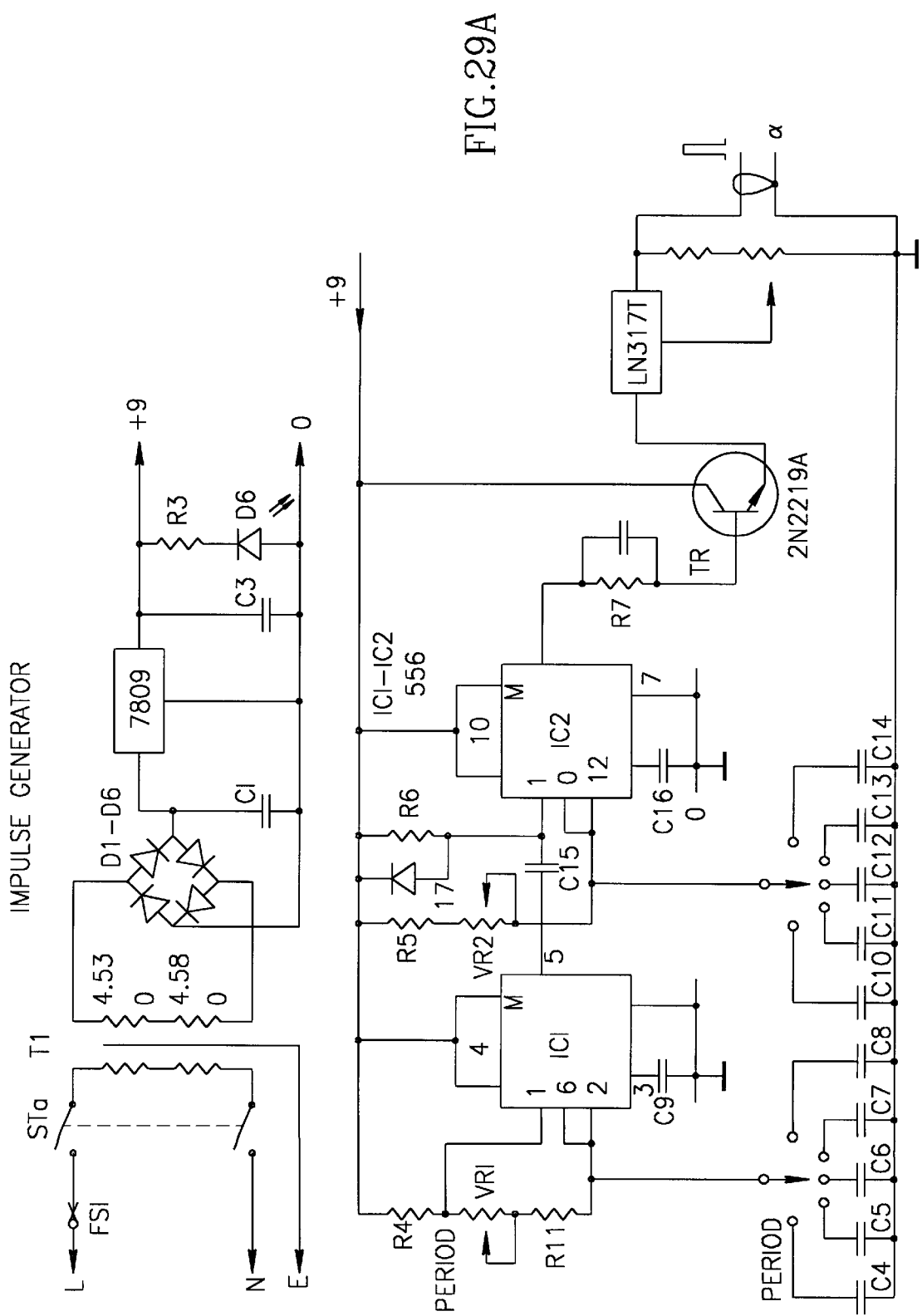
FIGS. 29(a)–29(B).
Figure 29B:
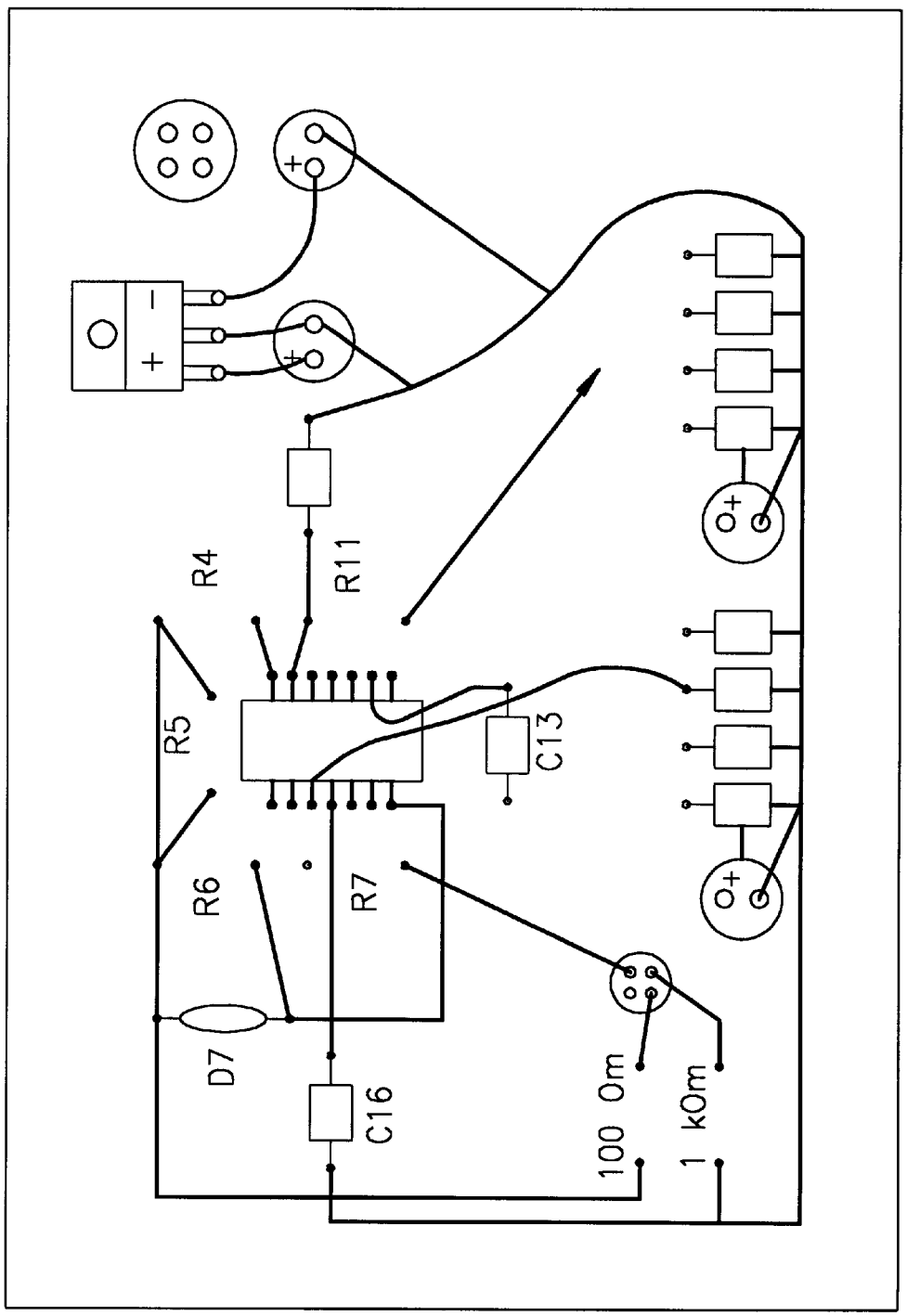

In another embodiment the signal generator is a pressure signal generator; said signal sensor is a pressure signal sensor; and said processor unit is operative to receive a heart beat signal; and synchronize receipt of said probe signal with said heart beat signal. As contemplated herein, the signal sensor includes at lest two sensing transducers disposed in spaced apart relation. The signal sensor is movable between at least two positions relative to said tubular conduit system and said processor unit is operative to calculate a pressure wave velocity from signals received from said two positions. In another embodiment the signal sensor includes a signal conditioner. The signal may be derived from either one of the internally generated waveforms or excited electronically from a separate signal generator either a stand alone unit. A stand alone until is of the type suitable is a multifunction synthesizer model HP 8904A from HP Test and measurement Organization, a Hewlett-Packard company USA) or integrated within a system computer, otherwise used for data acquisition and anaylsis. For example, an electric impulse generator is shown in FIG. 29.

Figure 4:
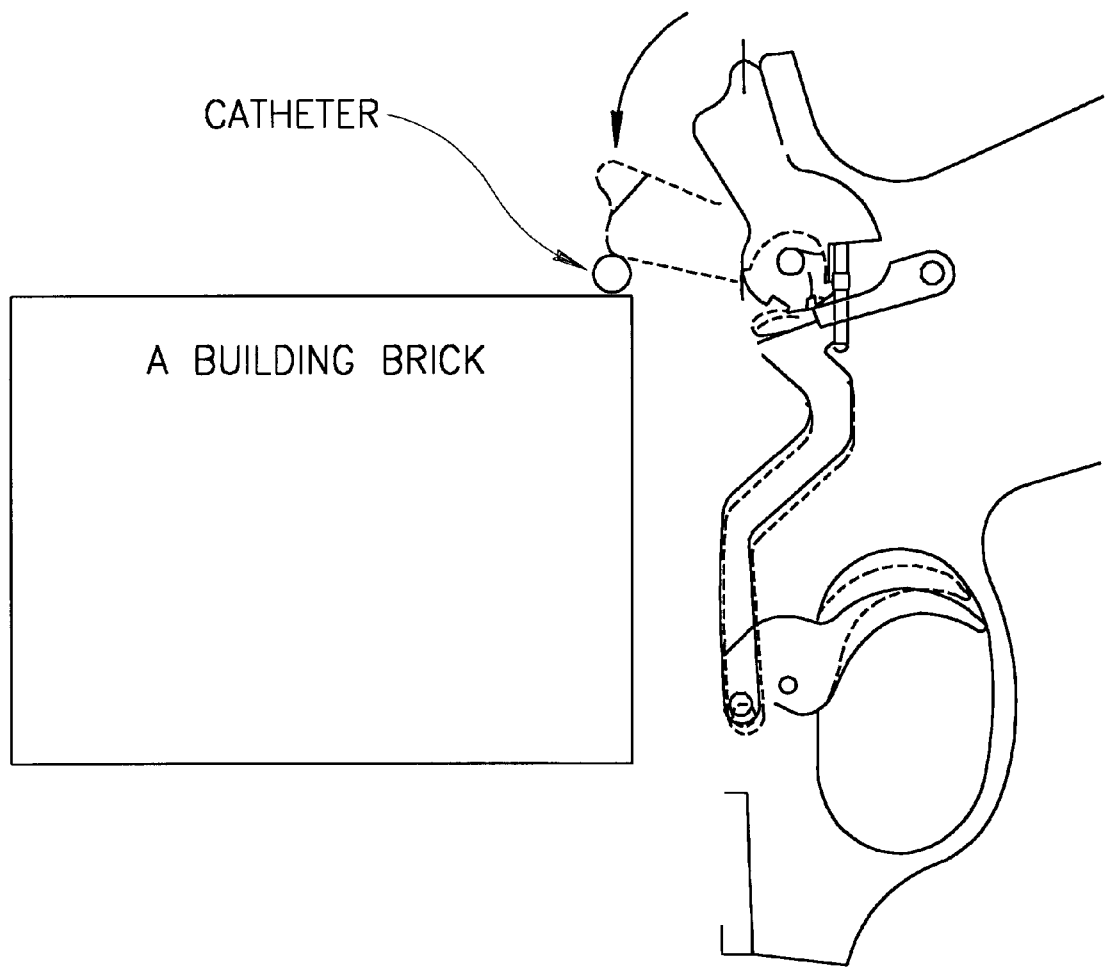
FIG. 4 is a schematic cross section illustrating one embodiment of the PSG unit 5 of FIG. 1 which was used in preliminary in-vivo studies.
Figure 8:
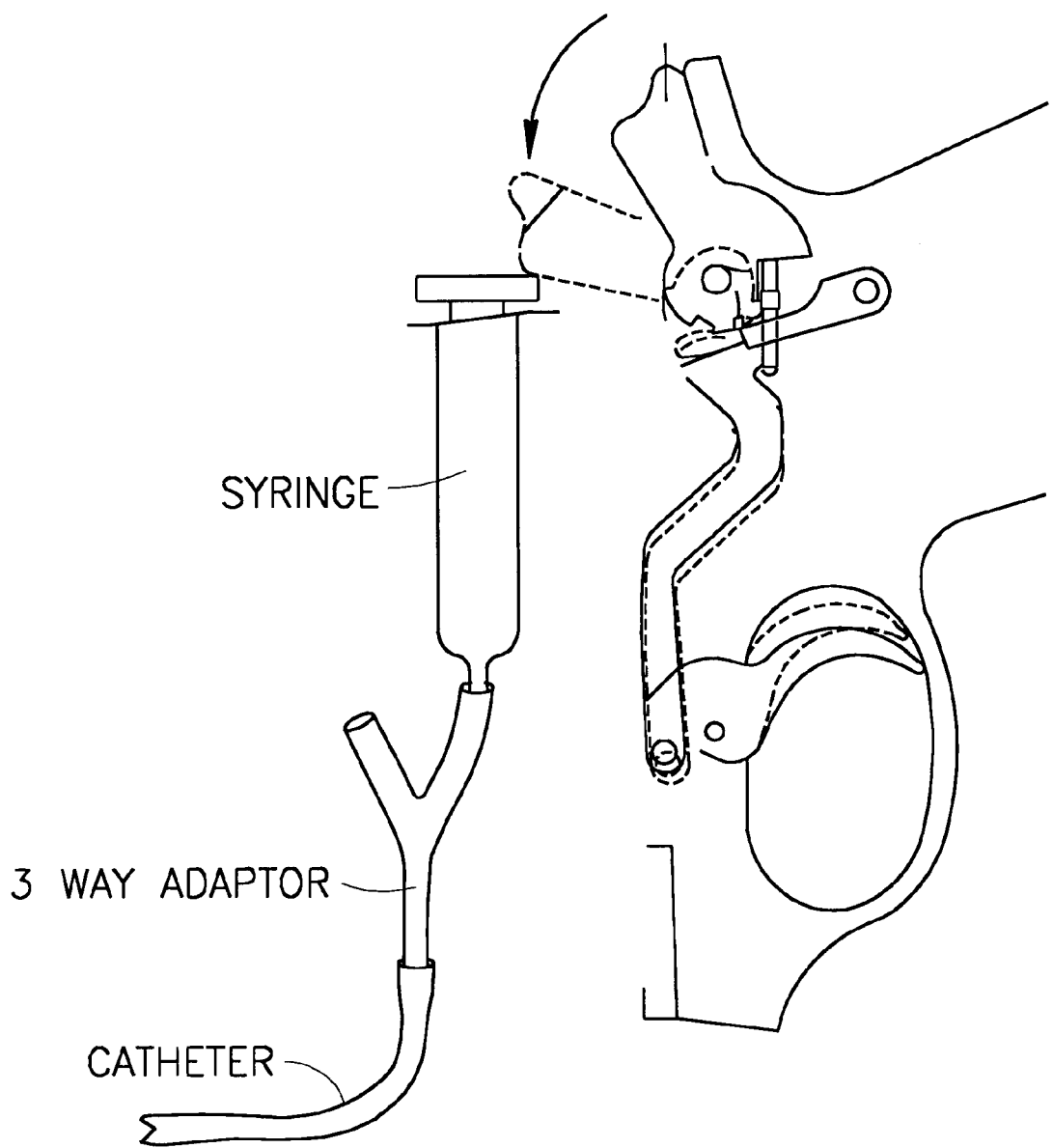
FIG. 8 is a schematic cross section illustrating one embodiment of the PSG unit 5 of FIG. 5 which was used in preliminary in-vitro studies.

In another embodiment the pressure signal may originate from an impact mechanism system. Such impact mechanisms are known to those skilled in the art. For example, the impact mechanisms may be of the spring loaded or electronically activated mechanical impact system types, applying pressure on either the catheter or on a container attached to it. A signal generation apparatus (in vitro and in vivo) of the impact mechanism type makes use of a pistol hammer mechanism, where the pistol hammer hits directly on the catheter, lying on a rigid surface, as shown in FIG. 4. The pistol used was a P230 semiautomatic pistol from Sig Sauer, Switzerland. Alternatively, the same pistol hammer hit the head of a standard 5 ml syringe, where the syringe was connected to the catheter through a standard manifold, as shown in FIG. 8.

The artificial pressure flow signal may also be synchronized with heart beats, either by gating to ECG or to system measurements a(pressure or flow) in which the ECG device measures heart heat signals upon reaching a desired time in the heart beat triggering the artificial pressure flow signal. The pressure signal dances through a catheter lumen into the blood vessel. The catheter may be a guiding catheter. A guiding catheter of the type suitable for this purpose is a 8F Archer coronary guiding catheter from Medtronic Interventional Vascular, Minneapolis, U.S.A. A diagnostic catheter of the type suitable for this purpose is a Siteseer diagnostic catheter, from Bard Cardiology, U.S.A. A balloon catheter of the type suitable for this purpose is a Supreme fast exchange PTCA catheter by Biotronik GMBH & Co, U.S.A. It will be appreciated by those skilled in the art that almost every hollow type catheter may be used. The presence of occlusion or aneurysm downstream creates reflection of pressure and flow waves. By extracting data of the reflected pressure waves, originated in the occluded site, the location and degree of occlusion can be determined using signal processing methods.

Additionally, the system can also be adopted for use in other non-biological conduits, having a pulsatile flow within, such as water pipes through which pulsatile flow may be induced for measuring and characterizing internal narrowing due to scale deposits. In another embodiment said tubular conduit system is a blood vessel system and said processor unit is operative to detect changes in arterial characteristics. In one embodiment the tubular conduit system is a urinary vessel system and said processor unit is operative to detect changes in urinary tract characteristics.

In another embodiment the probe signal is a plurality of discrete signals; said processor unit is operative to sample said discrete signals and receive pressure wave velocity data. The processor unit is operative to perform a single pressure function using said discrete signals and said pressure wave velocity data. The processor unit when performing said single pressure function is opeative to calculate an allpass value and a cepstrum value from said minimum phase component; separate a regular part and a singular part of said cepstrum value, where said singular part and said regular part from said pressure wave; calculate an exponential function of singular part; evaluate a second peak time delay with respect to a forward found in said pressure signal; evaluate a coefficient by calculation of a second peak amplitude to determine an arterial characteristic; evaluate a location of said arterial characteristic. The processor unit is operative to receive a forward pressure wave signal from a first transducer and a probe signal represented by a plurality of discrete signals sampled overtime. The processor until is operative to perform a dual pressure function.

In another embodiment said processor until when performing said dual pressure function is operative to: calculate an allpass component and cepstrum component of a minimum phase component of said forward pressure wave signal received from said signal sensor; apply an inverse filtering of said forward pressure wave signal; apply smoothing by a B-spline function; detect a forward peak location by a global maximum calculation; receive a threshold value; detect a second peak location by comparison with said threshold, where said threshold is derived from a forward peak maximum value and minimum size of a characteristic; evaluate a second peak time delay with respect to said forward peak; evaluate a reflection coefficient by calculating a forward and reflected peak area; and evaluate a location of said characteristic. The processor unit is operative to calculate a pressure wave velocity from a pressure wave sensed by said first and second transducers. In another embodiment the processor unit includes an analog to digital convertor. In another embodiment the processor unit is further operative to ascertain and assign a value corresponding to the location and size of said characteristic of said tubular conduit.

This invention provides a processor apparatus for detecting, locating and characterizing changes in a tubular conduit system within a living body for transferring fluids for use with a signal generator configured to transmit into said tubular conduit a probe signal that changes in response to encountering changes in said tubular conduit system and a signal sensor operative to receive said probe signal following transmission into said tubular conduit system, said processor apparatus comprising: a processor unit operatively connected to said signal sensor; a program for controlling the processor unit; said processor unit operative with said program to receive said probe signal following transmission through said tubular conduit system: identify changes in said probe signal; detect characteristics of said tubular conduit system, said characteristics of said tubular conduit system being derived from changes in said probe signal; recognize and assign a label said characteristic of said tubular conduit said system; and ascertain and assign a value corresponding to the location and size of said characteristic of said tubular conduit.

In one embodiment the processor unit is operative to select a method from a plurality of methods to identify changes in said probe signal and therefrom detect changes in said tubular conduit system. As contemplated herein, the processor unit is operative to detect aneurysms, stenosis, and/or arterial occlusions. In another embodiment, the tubular conduit system is a blood vessel system and said processor unit is operative to detect changes in arterial characteristics.

In another embodiment, the processor unit is operative to perform a single pressure function using said discrete signals and said pressure wave velocity data. In another embodiment, the processor unit when performing said single pressure function is operative to calculate an allpass value and a cepstrum value from said minimum phase component. In another embodiment, the processor unit when performing said single pressure function is further operative to separate a regular part and a singular part of said cepstrum value, where said singular part and said regular part form said pressure wave. In another embodiment, the processor until when performing said single pressure function is further operative to calculate an exponential function of singular part. In another embodiment, the processor unit when performing said single pressure function is further operative to evaluate a second peak time delay with respect to a forward found in said pressure signal. The processor until when performing said single pressure function is further operative to evaluate a coefficient by calculation of a second peak amplitude to determine an arterial characteristic. The processor unit when performing said single pressure function is further operative to evaluate a location of said arterial characteristic.

In another embodiment the signal generator is a pressure signal generator, and said signal sensor is a pressure signal sensor; said processing unit is operative to receive a heart beat signal; and synchronize receipt of said probe signal with said heart beat signal. In another embodiment the probe signal is a plurality of discrete signals; said processor unit is operative to sample said discrete signals and receive pressure wave velocity data.

In one embodiment the signal sensor includes two sensing transducers disposed in spaced apart relation and said processor unit is operative to receive a forward pressure wave signal from a first transducer and a probe signal represented by a plurality of discrete signals sampled overtime. The processor until is operative to calculate a pressure wave velocity from a pressure wave sensed by said first and second transducers. The processor unit is operative to perform a dual pressure function. In another embodiment, the signal sensor is movable between at least two positions relative to said tubular conduit system and said processing unit is operative to calculate a pressure wave velocity from signals received from said two positions.

In one embodiment the processor unit when performing said dual pressure function is operative to calculate an allpass component and cepstrum component of a minimum phase component of said forward pressure wave signal received from said signal sensor. In another embodiment, the processor until when performing said dual pressure function is further operative to apply an inverse filtering of said forward pressure wave signal. The processor until when performing said dual pressure function is further operative to apply smoothing by a B-spline function. The processor until when performing said dual pressure function is further operative to detect a forward peak location by a global maximum calculation. The processor unit when performing said dual pressure function is further operative to receive a threshold value. The processor unit when performing said dual pressure function is further operative to detect a second peak location by comparison with said threshold, where said threshold is derived from a forward peak maximum value and minimum size of a characteristic. The processor unit when performing said dual pressure function is further operative to evaluate a second peak time delay with respect to said forward peak. The processor unit when performing said dual pressure function is further operative to evaluate a reflection coefficient by calculating a forward and reflected peak area. The processor unit when performing said dual pressure function is further operative to evaluate a location of said characteristic. The processor unit is operative to calculate a pressure wave velocity from a pressure wave sensed by said first and second transducers.

This invention provides a method for using a computer to detect, locate and characterize changes in a tubular conduit system within a living body for transferring fluids wherein said computer is operatively connected to a signal generator configured to transmit into said tubular conduit a probe signal that changes in response to encountering changes in said tubular conduit system and a signal sensor operative to receive said probe signal following transmission into said tubular conduit system, said method comprising the steps of: receiving said probe signal following transmission through said tubular conduit system: identify changes in said probe signal; detecting characteristics of said tubular conduit system, said characteristics of said tubular conduit system being derived from changes in said probe signal; and recognizing and assigning a label said characteristic of said tubular conduit said system. In one embodiment the method includes the steps of ascertaining and assigning a value corresponding to the location and size of said characteristic of said tubular conduit. The method further includes selecting a process from a plurality of processes identifying changes in said probe signal and therefrom detecting changes in said tubular conduit system.

In one embodiment the tubular conduit system is a blood vessel system, said method further including detecting changes in arterial characteristics, detecting aneurysms, detecting stenosis, and/or detecting arterial occlusions.

In one embodiment the signal generator is a pressure signal generator, and said signal sensor is a pressure signal sensor; said method including receiving a heart beat signal; and synchronizing receipt of said probe signal with said heart beat signal. In another embodiment, the probe signal is a plurality of discrete signals; said method including sampling said discrete signals and receiving pressure wave velocity data. The method may include the steps of performing a single pressure function using said discrete signals and said pressure wave velocity data. Performing step includes the step of calculating an allpass value and a cepstrum value from said minimum phase component. Further, performing step includes the step of separating a regular part and a singular part of said cepstrum value, where said singular part and said regular part form said pressure wave. The step of calculating an exponential function of singular part. In another embodiment, the performing step includes the step of evaluating a second peak time delay with respect to a forward found in said pressure signal. In another embodiment the performing step includes the step of evaluating a coefficient by calculation of a second peak amplitude to determine an arterial characteristic. In another embodiment the performing step includes the step of evaluating a location of said arterial characteristic.

In one embodiment the signal sensor includes two sensing transducer disposed in spaced apart relation, said method includes the step of receiving a forward pressure wave signal from a first transducer and a probe signal represented by a plurality of discrete signals sampled overtime. In another embodiment the method further includes the step of calculating a pressure wave velocity from a pressure wave sensed by said first and second transducers. A dual pressure function may be performed. In another the signal sensor is movable between at least two positions relative to said tubular conduit system, said method including the step of calculating a pressure wave velocity from signals received from said two positions.

In another embodiment, the performing step includes the step of calculating an allpass component and cepstrum component of a minimum phase component of said forward pressure wave signal received from said signal sensor. In another embodiment the performing step includes the step of applying an inverse filtering of said forward pressure wave signal. In another embodiment, the performing step includes the step of applying smoothing by a B-spline function. In another embodiment the performing step includes the step of detecting a forward peak location by a global maximum calculation. In another embodiment the performing step includes the step of receiving a threshold value. In another embodiment the performing step includes the step of detecting a second peak location by comparison with said threshold, where said threshold is derived from a forward peak maximum value and minimum size of a characteristic. In another embodiment the performing step includes the step of evaluating a second peak time delay with respect to said forward peak. In another embodiment the performing step includes the step of evaluating a reflection coefficient by calculating a forward and reflected peak area. In another embodiment the performing step includes the step of evaluating a location of said characteristic. In another embodiment the performing step includes the step of calculating pressure wave velocity from a pressure wave sensed by said first and second transducers.

Figure 2:
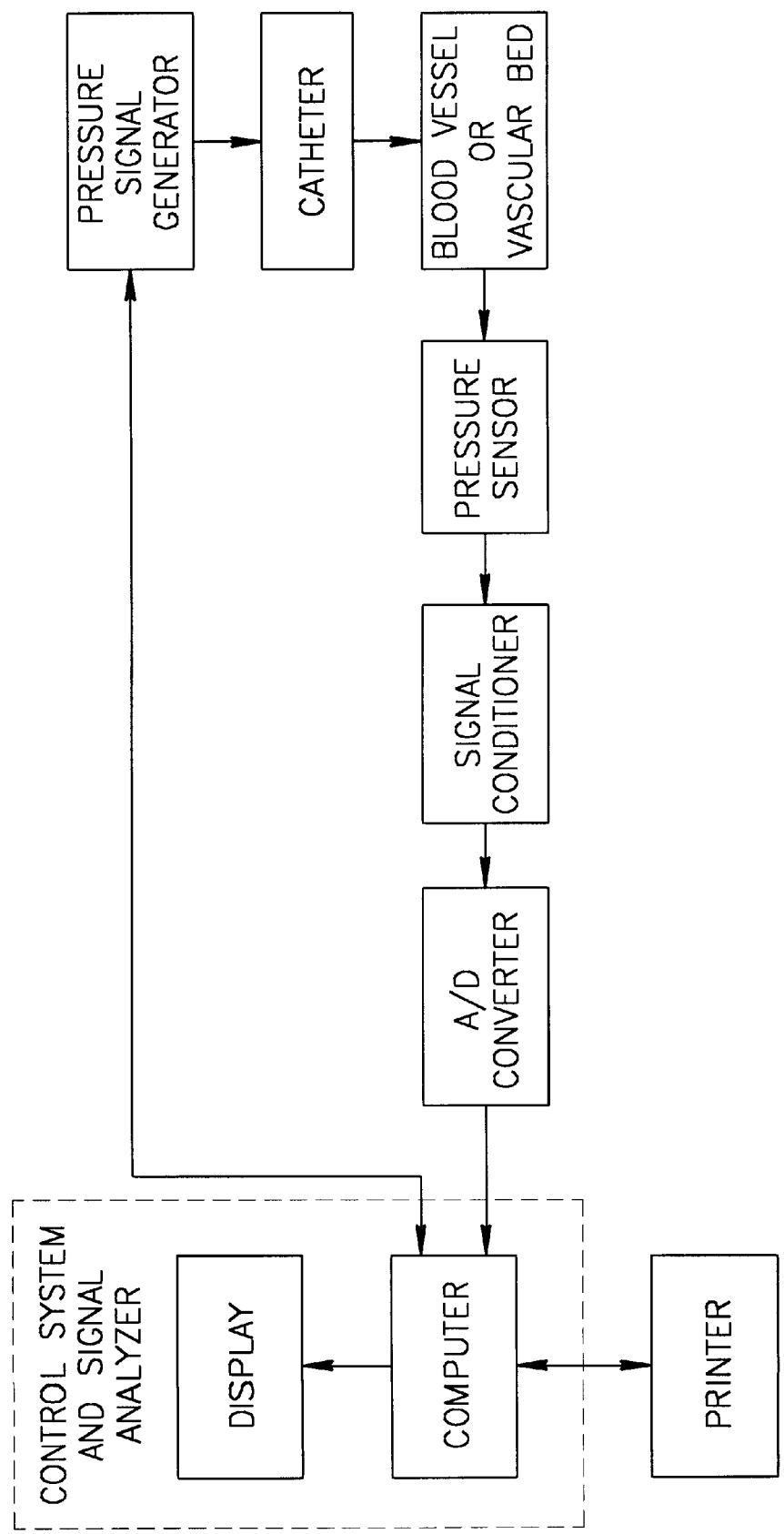
FIG. 2 is a schematic functional block diagram illustrating the details of clinical system 1 of FIG. 1.

With reference to the Figures for purposes of illustration, reference is now made to FIGS. 1 and 2. FIG. 1 is a schematic isometric view of a system for characterizing blood vessel occlusions, vascular bed and blood vessel walls constructed and operative in accordance with one embodiment of the present invention. FIG. 2 is a schematic functional block diagram illustrating the details of the system 1 of FIG. 1.

The system 1 includes a signal conditioner 23, such as a model TCB-500 control unit commercially available from Millar Instruments, a Radi Pressure Wire Interface Type PWI10, Radi Medical Systems, Upsala, or other suitable signal conditioner. The signal conditioner 23 is operatively connected to the pressure sensor 4 for amplifying the signals of the pressure sensor. The system 1 further includes an analog to digital (A/D) converter 28 connected to the signal conditioner 23 for receiving the conditioned analogs signals therefrom. The system 1 also includes a signal analyzer 20 connected to the A/D converter 28 for receiving the digitized conditioned pressure signals from the A/D converter 28. The signal analyzer 20 includes a computer 25, and optionally a display 21 connected to the computer 25 for displaying text numbers and graphs representing the results of the calculations performed by the computer 25 and a printer 26 operatively connected to the computer 25 for providing hard copy of the results for documentation and archiving. The A/D converter 28 can be a separate unit or can be integrated in a data acquisition computer card installed in the computer 25 (not shown). The computer 25 processes the pressure data which is sensed by the pressure sensors 4 and acquired by the A/D converter 28 or the data acquisition card (not shown) and generates textual, numerical and/or graphic data that is displayed on the display 21.

Another embodiment of the system 1 is a single unit containing both PSG and data acquisition, analysis and display, with or without correlation to ECG input. The system 1 includes a pressure catheter (or a pressure guidewire) 2 having a pressure sensor 4 attached thereto for measuring the pressure inside a blood vessel. In an exemplary embodiment, the pressure catheter 2 can be the 3F "one pressure sensor" model SPC-330A commercially available from Millar Instruments Inc., TX, U.S.A., or any other pressure catheter suitable for diagnostic or combined diagnostic/treatment purposes such as the 0.014" guidewire mounted pressure sensor product number 12000 from Radi Medical Systems, Upsala, Sweden, or Cardiometrics Wave Wire pressure guidewire from Cardiometrics Inc. an Endsonics company of CA, U.S.A.

It will be appreciated by those skilled in the art that the pressure and/or flow wave signals described herein each have a pressure and flow wave component. Such waves also produce distension of the vessel wall. For purposes of understanding, distension characteristics in general are most commonly visualized by observing a snake swallow and digest a large animal. Therefore, a pressure sensor, flow wave sensor or changes in the cross-sectional area or diameter measured over time can be used to collect data in connection with the procedures of the present invention.

Thus, another embodiment of system 1, includes a pressure or flow wave generator and a flow wave sensor 4. A flow wave sensor of the type suitable for this purpose are the Flowwire catheters manufactured by Endosonics Corporation, U.S.A. in which the system uses doppler ultrasound technology to accurately measure arterial blood flow velocity providing functional lesion assessment. Such device provide for measurements suitable for the procedures of the present invention as sold commercially or preferably when modified to allow for frequency increases to 200 Hz.

Accordingly another embodiment of the system 1 includes a pressure or flow wave signal generator and signal sensor adapted to changes in the cross-sectional diameter of the vessel caused by distension. A device suitable for this purpose is an intravascular ultrasound device of the type sold by Endosonics, USA having IVUS, Visions five 64 catheter catalog number 82700 together with IVUS Oracle In vision TM imaging system catalog number S7700470-inv. The IVUS data is measured while an artificial flow/pressure signal is introduced into the vessel. Other intravascular ultrasound systems provide diameter measurement at higher frequency and may be more easily processed at shorter distances of occlusion from sensor. A device of this type is an IRL VasoScan system, available from Intravascular Research Limited, Britain. The IRL VasoScan™ Pullback Sensor is an elegant simple innovation that facilitates lesion length measurement. AS the catheter is passed through the pullback device, the sensor measures movement both forward and backward. The user manually controls the device without sacrificing measuring accuracy. Measurements are displayed digitally on a system screen.

In another embodiment the signal generator is a pressure or flow signal generator and said signal sensor is a non-invasive high accuracy echo tracking Radio Frequency—ultrasound. A device this type is Model No. CFM-800c Ultrasound scanner produced by VINGMED, Norway, a General Electric company. This type of measurement provides basically the raw ultrasound data, prior to preprocessing and image processing. Therefore it may be available from other ultrasound scanners with some hardware and or software work. Other devices may include Model No. HP SONOS 5500 Cardiovascular Ultrasound System from Hewlett Packard, USA or Model No. HDI-5000 system from ATL, Seattle, USA (a Phillips company). The non-invasive ultrasound data is measured externally while an artificial flow/pressure signal is introduced into the vessel.

Figure 3:
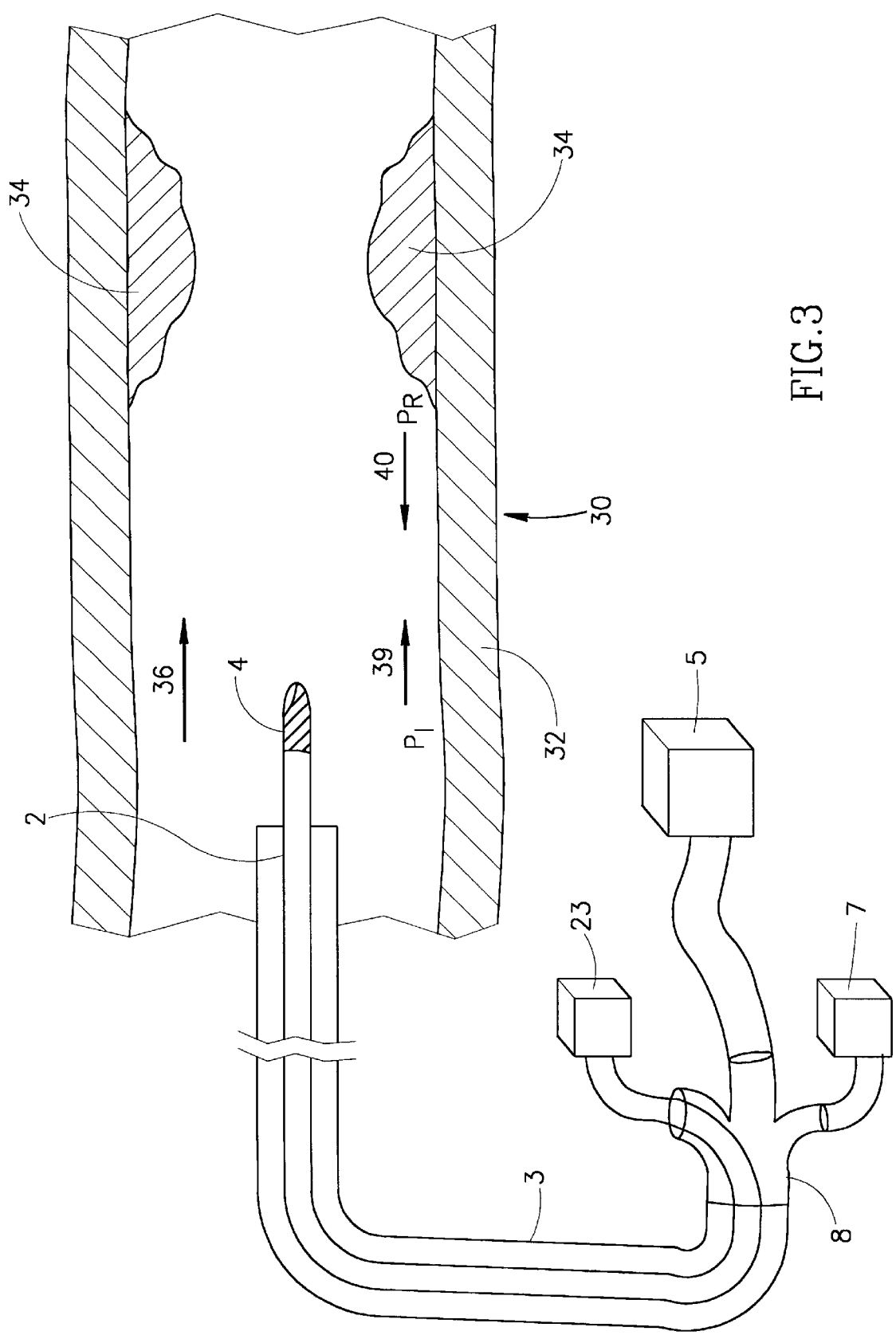
FIG. 3 is schematic cross section illustrating the positioning of the sensors, the pressure signal generator (PSG) and the catheter of the system 1 of FIG. 1 within an obstructed blood vessel during the operation of the system.

Reference is now made to FIG. 3. FIG. 3 is a schematic cross section illustrating the positioning of the guiding or diagnostic catheter 3 through which the pressure signal travels, relative to an obstruction and vascular bed within an occluded blood vessel during operation of the system 1 of FIG. 1.

The guiding catheter (or diagnostic catheter) 3 together with the pressure catheter or guidewire 2, to which the pressure sensor 4 is attached, are inserted into the vascular system of the patient using a standard connector 8 and standard methods and moved to reach the blood vessel of interest. FIG. 3 illustrates a cross section of an artery 30 having an arterial wall 32. The artery 30 also includes a stenotic obstruction 34 obstructing the blood flow through the artery 30. The degree of obstruction is defined as the ratio of the cross-sectional area of the stenotic region to the cross-sectional area of the unobstructed artery (not shown). The cross-sectional area of the stenotic region is the cross-sectional open area at the narrowest part of the occlusion. The obstruction distance is defined as the distance between the measuring point of the pressure sensor 4 to the narrowest cross-section of the obstruction (not shown). In some of the methods presented below, two pressure measurements are required. In those cases, the proximal measurement my be collected using a pressure transducer 7 (e.g. Baxter Model PX272, pressure monitoring kit from Baxter Healthcare Corporation, Ca, U.S.A.), connected to the guiding catheter of system 1 via the connector 8, or a second intravascular pressure transducer, or the two single pressure sensors may be mounted on a mutual wire or catheter (e.g. Millar 2.5F dual sensor model SPC-721, Millar Instruments Inc., TX, U.S.A.).

The pressure catheter 2 is advanced within the artery 30 proximal to the obstruction 34 in the direction of the arterial blood flow indicated by the arrow labeled 36, or opposite. PSG 5 creates a pressure signal, either synchronized with natural beats (ECG) or not, represented by the arrow 39 labeled $P_1$. $P_M(t)$ is the combination of the incident pressure wave, and the reflected pressure wave $P_R$ (pressure signal reflected by the stenosis 34), represented by the arrow 40 labeled $P_R$, which was reflected from the obstruction at a time (t–τ), wherein τ is the time delay between the forward pressure wave and the reflected pressure wave, read by the transducer. Following, several methods will be presented, serving for distinguishing $P_1$ from $P_R$ while measuring $P_M(+)$, calculating τ and while knowing PWV determining distance to the reflecting site (either stenosis or VB or both). Several methods for calculating the location and reflection coefficient $R_F$ of the stenosis are presented. Several methods for calculating the pressure wave velocity are presented. The main geometrical parameter of a stenosis is stenosis severity As/Ao. Here As is the minimum open cross-sectional area of the stenosis and Ao is the nominal cross-sectional area of the unobstructed vessel. In one model for pressure drop across stenosis, suggested by Young and Tsai (Young D. F. and Tsai F. Flow characteristics in model of arterial stenoseses -II. Unsteady flow. J.Biomechanics 6, 547–559, 1973.), allows to relate reflection coefficient to geometrical parameters of the stenosis, characteristics of the excited pressure wave and input impedance of the blood vessel. The related equations may be found in the work N. Stergiopulos, M. Spiridon, F. Pythoud, J. J. Meister. On the wave transmission and reflection properties of the stenosis. J.Biomechanics, v.29, No.1, pp. 31–38, 1996. In the general case, stenosis severity As/Ao and stenosis length L may be found only if reflection coefficient is known for different frequencies. Therefore, in the general case the reflection of the exciting pressure signal containing different frequencies must be measured. Another possible way is to determine one of the geometrical parameters (stenosis length or stenosis severity) from QCA. The other parameter may be calculated from the measured reflection coefficient.

For short lesions the reflection coefficient is directly related to stenosis severity and the pressure excitation signal. The same principle holds for flow and velocity measurements. A good approximation of the reflection coefficient, based on the linearized flow theory is given by the following relation: $R_F=(Ao-As)/(Ao+As)$. This relationship holds for short distances where signal attenuation is not significant. For long range stenoses the calculation should correct for the attenuation of the pressure excitation signal and its reflections.

The present invention discloses a device and a method for a quantitative determination of the elastic properties of blood vessels for characterizing, inter alia, the real part of the complex Young modulus, the distensibility and the compliance of lesioned and non-lesioned parts of blood vessels. The derived elastic properties may be further used to determine the degree of calcification of lesioned and non-lesioned parts of blood vessels. These parameter values can be calculated and reported in absolute terms as a ratio of the relevant parameter value in the lesion region to the parameter value in a non-lesion region of the same patient. Alternatively, the system may calculate and report a ratio of the relevant parameter determined in the lesion region of the patient to a "standard" average value of the relevant parameter as measured in a group of healthy people with similar physiology (age group, gender, vessel type, etc.). In the second alternative, the system will include means for storing such standard average values of the relevant parameters such as a data-based stored in a suitable storage device included in the system (not shown).

Figure 5:
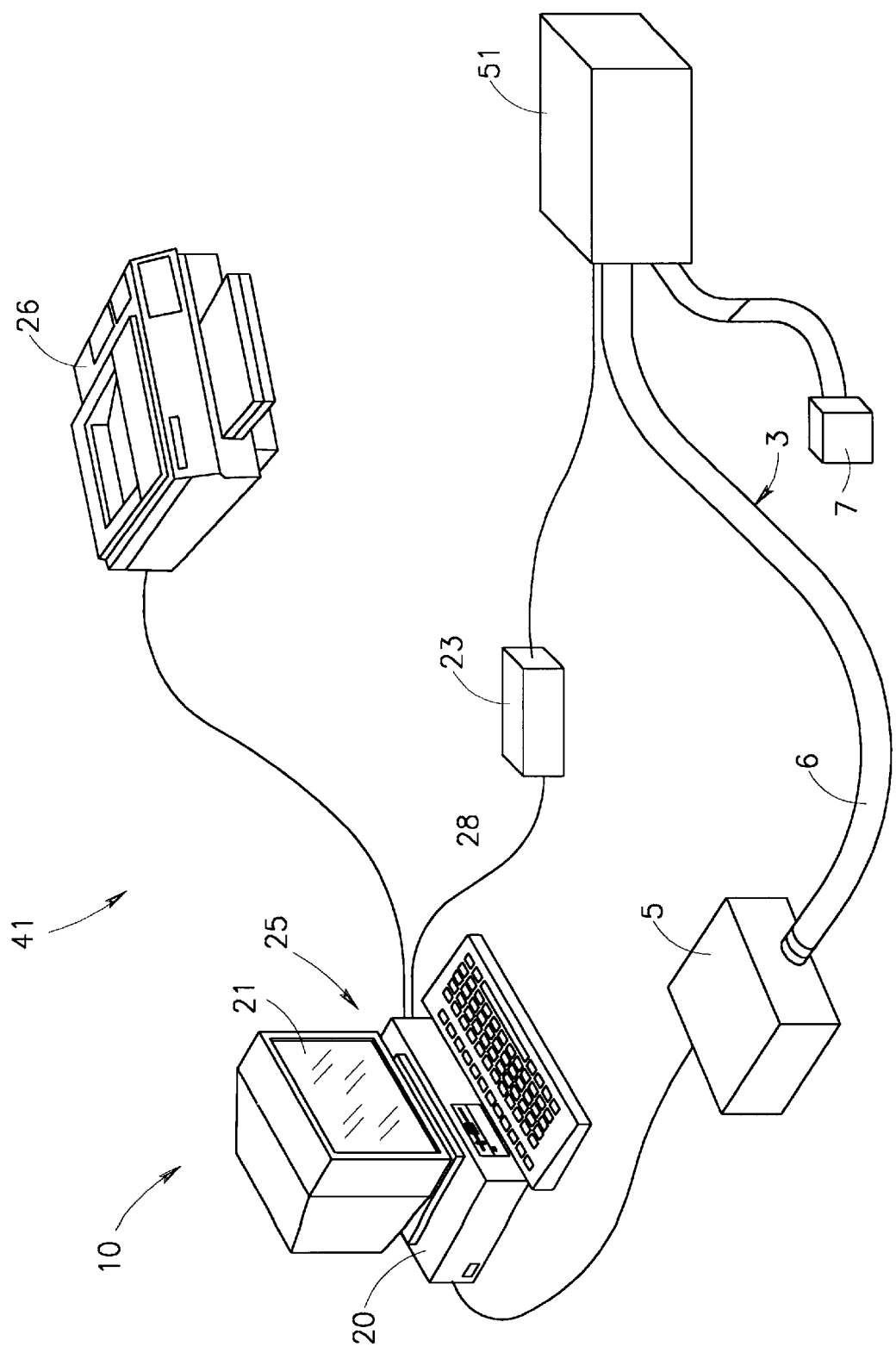
FIG. 5 is a schematic view of an in-vitro system used for characterizing lesions, aneurysm or vascular bed in blood vessels.
Figure 6:
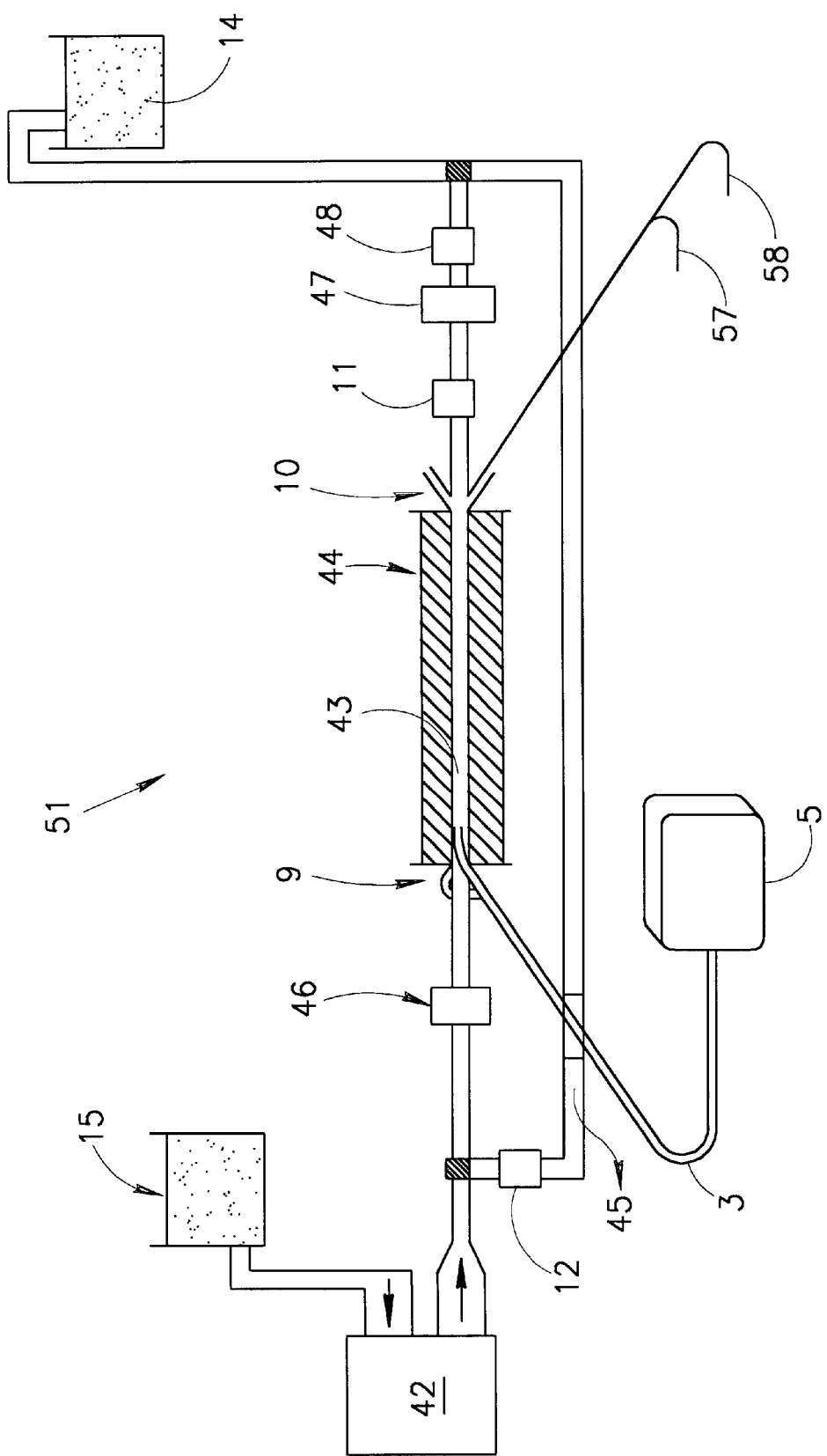
FIG. 6 is schematic cross section illustrating the in-vitro recirculating system 51 of system 41 of FIG. 5.
Figure 7:
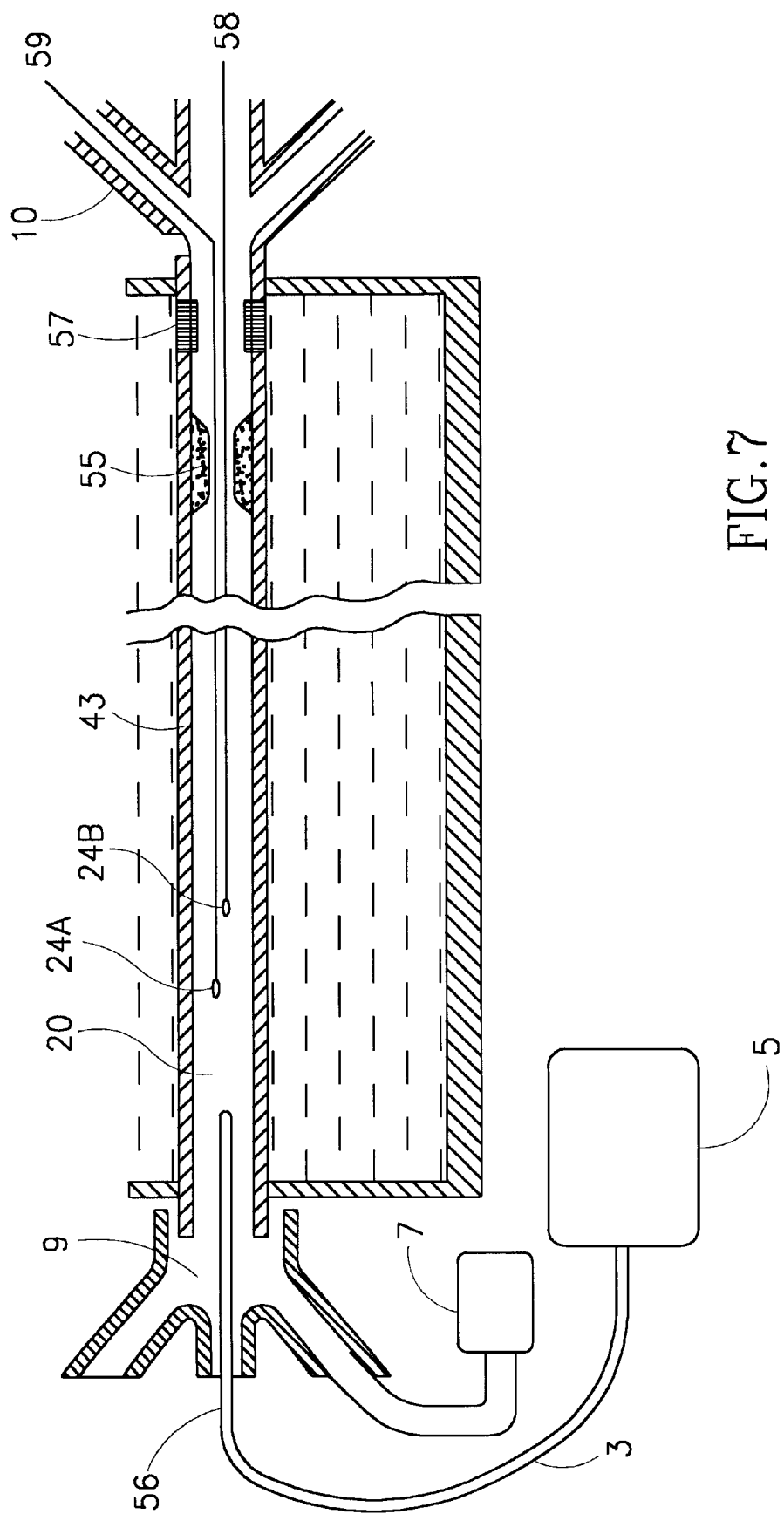
FIG. 7 is schematic cross section illustrating the positioning of the sensors, the pressure signal generator (PSG) and the catheter of the system 51 of FIG. 6 during the operation of the system.

The determination of the elastic properties of an artery is based on calculating the phase velocity of the pressure wave. Reference is now made to FIGS. 5–7. FIG. 5 is a schematic diagram representing an in-vitro experimental apparatus constructed and operative for determining flow characteristics in simulated non lesioned and lesioned blood vessels, in accordance with an embodiment of the present invention. FIG. 2 is a schematic functional block diagram illustrating the functional details of a system including the apparatus of FIG. 5 and apparatus for data acquisition, analysis and display.

Reference is now made to FIG. 5. The system 41 includes the system 51. The system 41 also includes a signal conditioner 23. A conditioner of the type suitable for this purpose is a model TCB-500 control unit commercially available from Millar Instruments, or any suitable signal conditioner. The signal conditioner 23 is operatively connected to the pressure sensors 24A and 24B for amplifying the signals of the pressure sensors 24A and 24B. The system 41 further includes an analog to digital (A/D) converter 28 connected to the signal conditioner 23 for receiving the conditioned analog signals therefrom. The system 41 also includes a signal analyzer 20 connected to the A/D converter 28 for receiving the digitized conditioned pressure signals from the A/D converter 28. The signal analyzer 20 includes a computer 25, a display 21 connected to the computer 25 for displaying text numbers and graphs representing the results of the calculations performed by the computer 25 and a printer 26 operatively connected to the computer 25 for providing hard copy of the results for documentation and archiving. The A/D converter 28 can be a separate unit or can be integrated in a data acquisition computer card installed in the computer 25 (not shown). The computer 25 processes the pressure data which is sensed by the pressure sensors 24A and 24B and acquired by the A/D converter 28 or the data acquisition card (not shown) and generates textual, numerical and graphic data that is displayed on the display 21.

The fluidics system 51 of FIG. 6 is a recirculating system for providing pulsatile flow. The system 51 includes a pulsatile pump 42. A pump of the type suitable for this purpose is a model 1421A pulsatile blood pump, commercially available from Harvard Apparatus, Inc., Ma, U.S.A., however other suitable pulsatile pumps can be used. The pump 42 allows control over rate, stroke volume and systole/diastole ratio. The pump 42 recirculates distilled water from a water reservoir 15 to a water reservoir 14.

The system 51 further includes a flexible tube 43 immersed in a water bath 44, to compensate for gravitational effects. The flexible tube 43 is made from Latex and has a length of 120 cm. The flexible tube 43 simulates an artery. The flexible tube 43 is connected to the pulsatile pump 42 and to other system components by Teflon tubes. All the tubes in system 51 have 4 mm internal diameter. A bypass tube 45 allows flow control in the system and simulates flow partition between blood vessels. A Windkessel compliance chamber 46 is located proximal to the flexible tube 43 to control the pressure signal characteristics. A Windkessel compliance chamber 47 and a flow control valve 48 are located distal to flexible tube 43 to simulate the impedance of the vascular bed. The system 51 of FIG. 5 further includes an artificial stenosis made of an artificial stenosis section 55, inserted within the flexible tube 43. The tube section 55 is made from a piece of Teflon tubing. The internal diameter 52

(not shown) of the artificial stenosis 55 may be varied by using artificial stenosis sections fabricated separately and having various internal diameter. The external diameter of all the artificial stenosis section 55 is 4 mm. Thus, various degree of cross sectional area reduction (40%–95%) can be generated in the distal part of the flexible tube 43, for simulating various degrees of stenosis.

Reference is now made to FIG. 7, which is a schematic cross sectional view illustrating a part of the fluidics system 51 in detail. Pressure is measured along the flexible tube 43 using a pressure measurement system including MIKRO-TIP pressure catheters 58 and 59, such as the model SPR-524 pressure catheter, connected to a model TCB-500 control unit, both commercially available from Millar Instruments Inc., TX, U.S.A. The catheters 58 and 59 are inserted into the flexible tube 43 via the connector 10, connected at the end of the flexible tube 43. The catheters 58 and 59 include pressure sensors 24A and 24B, respectively, for pressure measurements. It is noted that, other catheters or guide wires made by different manufacturers may also be used, such as various pressure measurement guide wires of the type commercially available from Radi Medical Systems AB, Upsala, Sweden, or from Cardiometrics, an Endosonics company of CA, U.S.A.

The end of catheter 3 is inserted into the flexible tube 43 via a connector 9. The other end is connected to a pressure signal generator unit 5, which creates pressure impulse. The pressure wave advance in the fluid through the catheter 56 to vessel 43. When the pressure wave reaches the artificial stenosis 55, reflection of the pressure wave is created. The pressure sensors 24A, 24B measure the original pressure wave and the reflections from the artificial stenosis, and other reflections of the system such as the reflection from the right flexible tube edge 57. A fluid filled pressure transducer 7 is connected to the system 51 via the connector 9, when additional pressure readings are needed, or in place of a second intravascular pressure transducer, when two pressure measurements are of interest.

The system 51 of FIG. 6 also includes a flowmeter 11 connected distal to the flexible tube 43 and a flow meter 12 connected to the bypass tube 45. The flowmeters 11 and 12 are operatively connected to the A/D converter 28. The flowmeters 11 and 12 are model 111 turbine flow meters of the type commercially available from McMillan Company, TX, U.S.A. However, other commercial available flow sensors may be used.

EXPERIMENTAL DETAILS SECTION

Data acquisition and analysis:

Data acquisition was performed using a PC (Pentium 586) with an E series multifunction I/O board 28 model PC-NIO-16E-4 of the type commercially available from National Instruments Inc., TX, U.S.A. The I/O board was controlled by a Labview graphical programming software, commercially available from National Instruments Inc., TX, U.S.A. 10 sec interval of pressure and flow data were sampled at 5000 Hz, displayed during the experiments on the monitor and stored on hard disk. Analysis was performed offline using Matlab version 5 software, commercially available from The MathWorks, Inc., MA, U.S.A.

System Implementation Methods and Procedures:

The system uses various methods to detect the existence, location and severity of a stenosis or aneurysm in a blood vessel. The methods are based on four main data analysis procedures which are described hereinbelow. Other data analysis procedures may be developed based on the principles hereinbelow presented. The choice between procedures depends on the signal length and distance from the lesioned area. These two parameters define the time of the reflection within the signal the amount of separation between the forward and backward signal serves to select the proper procedure. In the data presented hereinbelow, acquired on the in-vitro system presented in FIGS. 4–6, and with pressure wave velocity of 14 m/sec, three different cases were defined: far distance (over 40 cm), mid distance (10–40 cm) and short distance (2–10 cm) stenoses. Usually, far and mid distance stenoses were found using the Procedure 1 presented below. Short distance stenosis were identified using both Procedure 1 and 2 presented below. As well, in vivo pig data is included, identifying induced occlusions.

PROCEDURE 1

The Dual Pressure Function

The following procedure analyzeD a downstream pressure measurement, composed of both forward and reflected waves, by a priori knowledge of the forward wave. It was determined from:

a. an upstream measurement, either simultaneously (additional transducer) or non simultaneously [moving the transducer] or b. a priori knowledge of forward pressure wave, resulting from known pressure excitation with known catheter Input data required for the procedure:

1. The forward pressure wave, w[n].
2. The pressure measured by a downstream sensor—s[n], n=1, . . . N, where N is the number of samples.

Assumptions:

1. All measured signals are discrete-time signals.
2. The vessel is a linear, stable and time-invariant causal system.
3. The time resolution of the linear system is much less then the time delay of the reflected pressure wave.
4. Reflection coefficient is a constant.
5. Exciting signal (forward pressure wave) is known.
6. The pressure wave velocity V is known. The pressure wave velocity may be calculated with Procedure 3, or assumed to be known from previous test data. It also was known from anatomic data, according to exact vessel, age and clinical situation.

Experiment setup:

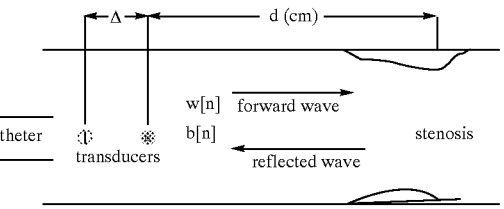

Procedure description:
The following relationship holds:

$$s[n]=w[n]+b[n-m]=w[n]\otimes(\delta[n]+r*g[n-m]); \qquad (1)$$

where, $\otimes$—is the discrete convolution operator;

s[n]—is the measured pressure wave;

w[n]—is the forward pressure wave;

b[n]=r*g[n]⊗w[n]—is the reflected pressure wave;

d—is the distance between the downstream sensor to the stenosis;

g[n]—is the response of the vessel in 2d length (to the stenosis and back);

r—is the reflection coefficient;

m=round (2*d/v)—is the time delay (in samples) of the reflected pressure wave;

v—is the pressure wave velocity;

Δ—is the distance between transducers.

Using the commutative property of the convolution, Equation (1) describes a digital linear filter:

$$\delta[n] + r*g[n-m]w[n]s[n]$$

where w[n] represents the impulse response of this filter.

The parameters r and m of the reflected wave describe the stenosis size and location. Therefore, in order to evaluate the stenosis we need to evaluate the reflected wave parameters. In the common case, it is impossible to detect the reflected wave and evaluate its parameters by inspecting the signal s[n]. In order to get information about the reflected wave inverse filtering to the measured pressure wave was applied:

$$\delta[n]+r*g[n-m]=w^{-1}[n] \otimes s[n].$$

The result is a function including two peaks representing the forward and reflected pressure wave and having different amplitudes. The first maximum is equal to 1 and the second one is r. The time difference between the peaks is the reflected pressure wave delay.

As the output signal s[n] includes measurement noise, smoothing filter h[n] should be applied prior to the inverse filtration:

$$h[n]\otimes(w^{-1}[n])=h[n]\otimes(\delta[n]+r*g[n-m])=h[n]+r*(h[n]\otimes g[n-m])$$

Since it was assumed that w[n] is known, the Minimum-Phase/Allpass decomposition was obtained by iterative procedure described by Tarasov R. P. (Comput.Maths.Math.Phys., Vol.32,No.10,pp.1373–1390, 1992), The computation of functions in the algebra of formula polynomials and multidimensional digital signal processing procedures.

w[n]=u[n]⊗ exp (k[n]), where u[n]—is the Allpass component;

exp (k[n])—is the Minimum-Phase component;

k[n]—is the cepstrum of a Minimum-Phase component.

Once u[n] and k[n] are evaluated, the inverse filter of the measured pressure wave s[n] is h[n]:

$$h[n]+r*(h[n]\otimes g[n-m])=h[n]\otimes(u[-n]\otimes \exp(-k[n])\otimes s[n])(2).$$

For final smoothing purpose B-spline was used.

Procedures steps:

Step 1: Input: w[n]. The allpass component u[n] and the cepstrum k[n] of the minimum-phase component of the forward wave w[n] was calculated.

Step 2: inverse filtering by expression (2) was applied

Step 3: smoothing by B-spline was applied

Step 4: the forward peak location by global maximum calculation was detected

Step 5: the reflected peak location was detected by comparison with the threshold that depends on forward peak maximum $M_f$ and minimum stenosis size of interest.

Figure 17:
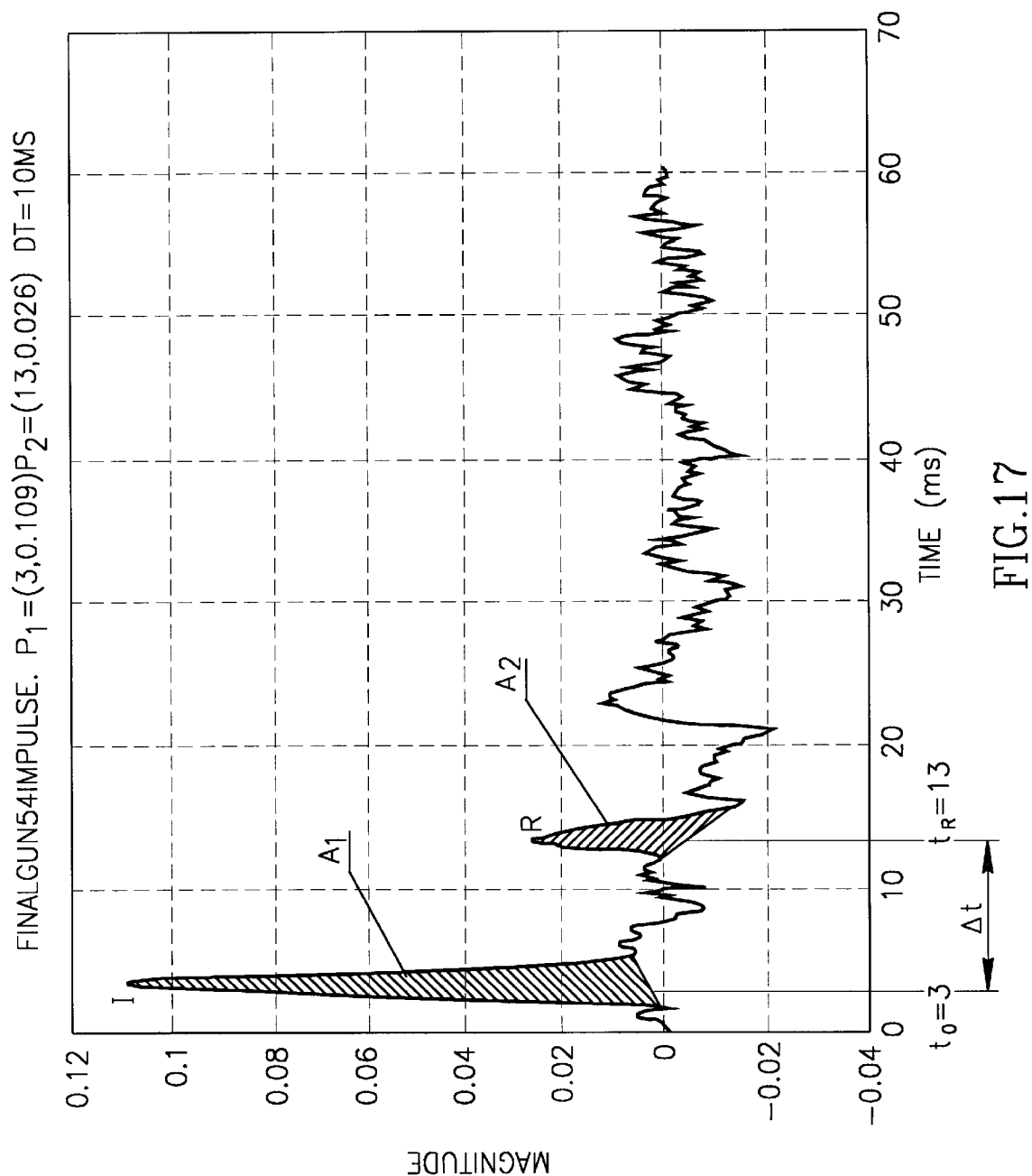
FIG. 17 is a demonstration of the calculation of the stenosis severity as the area ratio of the two peaks resulting from Procedure 1.

Step 6: the reflected peak time delay was evaluated with respect to forward peak by reflected peak shift m calculation: τ=m*f, where f is the sampling frequency Step 7: the reflection coefficient r was evaluated by calculating the forward and the reflected peak area. Reference is now made to FIG. 17. FIG. 17 presents the result of Procedure 1, where the first peak represents the input pressure pulse and the second peak represents the reflected pressure wave. The ratio of the area under those peaks serves to estimate the severity of the stenosis or aneurysm, according to the definition presented hereinabove.

Step 8: the stenosis location was evaluated by: d=v*τ/2

Figure 11:
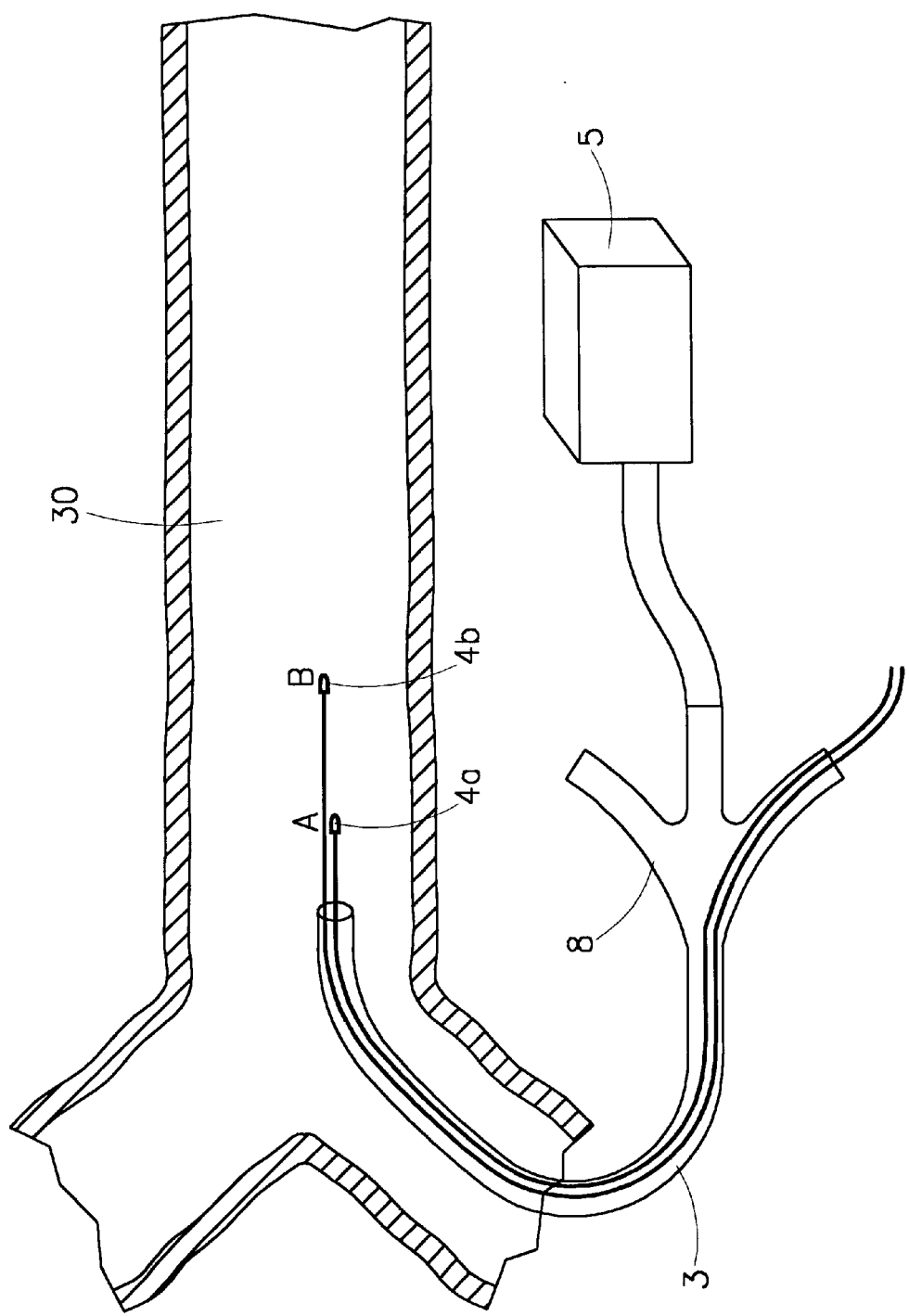
FIG. 11 is an isometric description of the setup used in Method 5 including the PSG unit, the two pressure sensors and the catheter within a blood vessel without stenosis.

In the above procedure, s(n) represents a pressure measurement at point B, as demonstrated in FIG. 11. W(n) was derived as:

1. A second pressure measurement, derived by a second pressure sensor, located upstream at location A—presented in Method 6.

2. A second pressure measurement derived with the same pressure sensor, moved to an upstream location, designated A—presented in Method 4.

3. A prior knowledge of the input signal (excitation signal and transfer function of the catheter)—presented in Method 3.

4. The initial part (in the time domain) of the pressure signal, s(n), for a long range stenosis, where a complete separation of the forward and backward signals occurs—presented in Method 2.

PROCEDURE 2

Single Pressure Function

Input data required for the procedure:

1. Pressure versus time function Pa[n]=Pa(Δt*n), n=1, . . . N, $$\frac{1}{\Delta t}$$

is the sampling frequency.

2. Pressure wave velocity. The velocity was assumed to be known from previous test data, or derived according to Procedure 4, presented below.

Procedure description:

If the exciting signal was unknown, the reflected wave parameters were evaluated by separating the regular ln w[n] and the singular p[n] of the ln s[n] where lns[n]≡$k_s$≈ln w[n]+p[n] and lnw[n]≡k[n], p[n]=

$$p[n] = \sum_{i=1}^{j}(-1)^{i+1}*r^i*\delta^i[n-i*m]/i, \delta^{i+1}[n]$$

$$= \delta^i[n] \otimes \delta[n-m], \delta^0[n] \equiv \delta[n].$$

where s[n]=w[n]+b[n-m]=w[n]⊗(δ[n]+r*g[n-m] is the measured pressure wave;

Procedure steps:

Step 1: the allpass component $u_s[n]$ and the cepstrum $k_s[n]$ of the minimum-phase component: $s[n]=u_s[n] \otimes \exp(k_s[n])$ was calculated.

Step 2: the regular lnw[n] and the singular p[n] part of the $k_s[n]$ were separated Step 3: the exponential function of the p[n]: $q[n]=\exp p[n]$ was calculated Step 4: the reflected (second) peak time delay τ with respect to forward peak: $\tau=m*f$, where f- is the sampling frequency was evaluated Step 5: the reflection coefficient r by calculation of the reflected amplitude, or area (as demonstrated in FIG. 17) was evaluated.

Step 6: the stenosis location by: $d=v*\tau/2$ was evaluated

PROCEDURE 3

Pressure Wave Velocity with Two Pressure Transducers

Simultaneous pressure measurements with two pressure transducers was determined as follows: the pressure wave velocity was derived as DL/Dt, where DL is the distance between the transducers and Dt is the time delay between corresponding points on the pressure-time curves as measured by the two transducers (for example, Dt at a time delay between pressure maxima may be used or alternatively, one may choose the time delay between points at which the pressure attains a fixed, arbitrarily chosen, percentage of the full range of the pressure curve (e.g. 10%)). The measured pressure rises very fast and in most cases it reaches its maximum before the reflected wave has had time to overlap the forward pressure wave. It is known, that the PWV in arterial segment increases with pressure, which is an indication of gradual stiffening of the artery with pressure. By using well established viscoelastic arterial models, the analysis of the PWV for several specified percentage of full range of the pressure enables one to computer the stiffness of the vessel wall.

PROCEDURE 4

Pressure Wave Velocity with One Pressure Transducer

PMV is calculated using a single pressure or flow transducer, measuring reflection time at two sites Ds cm apart. The reflection time, at each site, is found using one of the single pressure transducer methods described hereinbelow. Dt is the difference between the measured reflection times at these two points. The pressure wave velocity is then calculated as: PMV=2·Ds/Dt.

METHOD NO. 1: Single pressure sensor—unknown input signal

Figure 9:
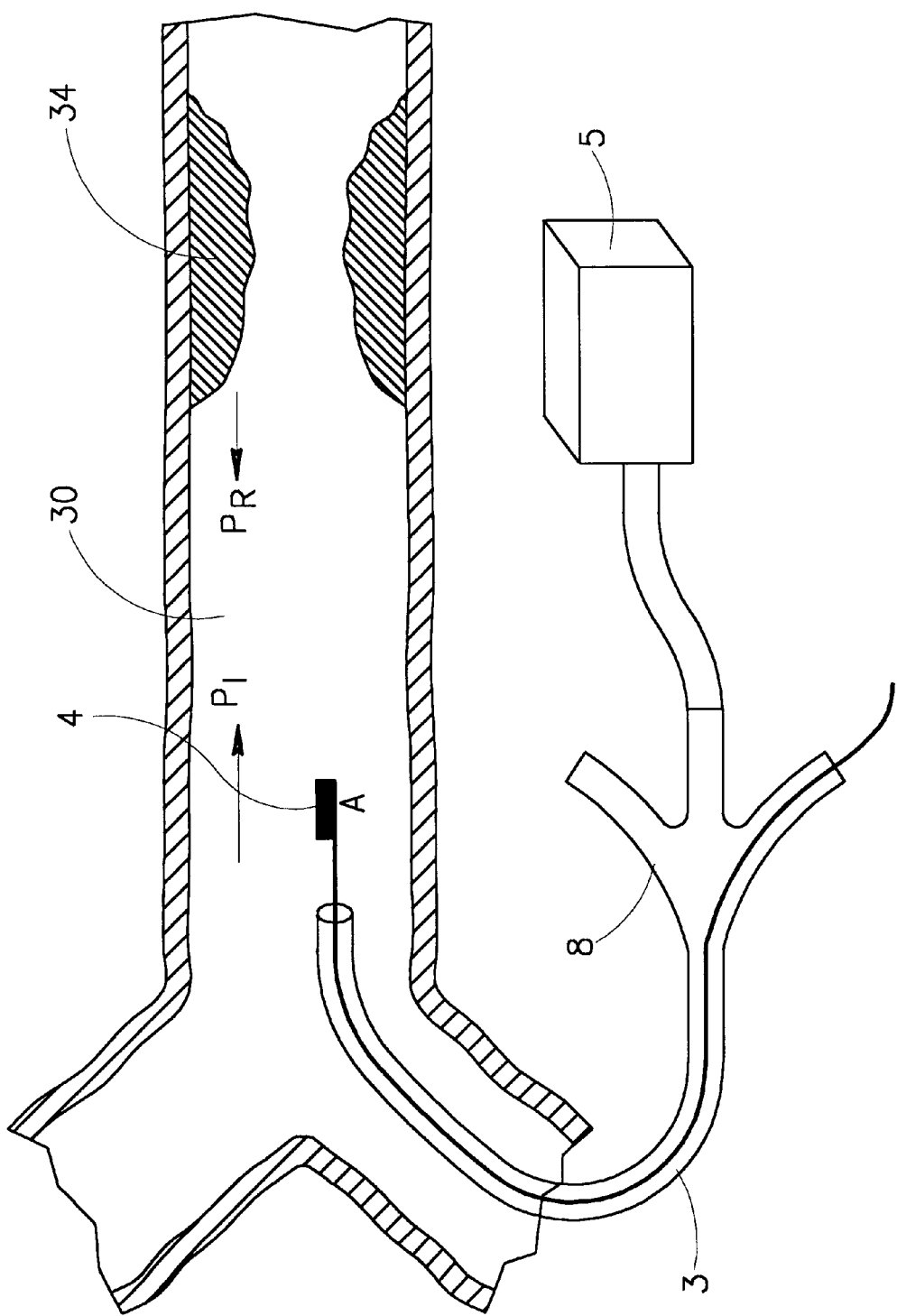
FIG. 9 is isometric description of the setup used in Method 1 including the PSG unit, the signal pressure sensor and the catheter within a blood vessel.

Reference is now made to FIG. 9. A single pressure sensor 4 is inserted into the blood vessel of interest 30 and positioned at point A. Pressure pulse is applied by the pulse generator 5 and data of pressure versus time Pa(t), at point A, are obtained. The applied pressure pulse is assumed to be unknown, or the applied pressure pulse is known but the transfer function of the catheter is unknown. Subsequently, the input pressure signal entering the blood vessel is unknown.

Data analysis

The system uses the single pressure function procedure (Procedure 2) to detect the existence and location of a stenosis, aneurysm or vascular bed.

Output Results

1. Location of stenosis, aneurysum or vascular bed.
2. Stenosis or aneurysm severity.
3. Pressure wave velocity. The velocity is calculated using Procedure 4 or assumed to be known from previous test data.

In-Vivo Experimental Results

Figure 10:
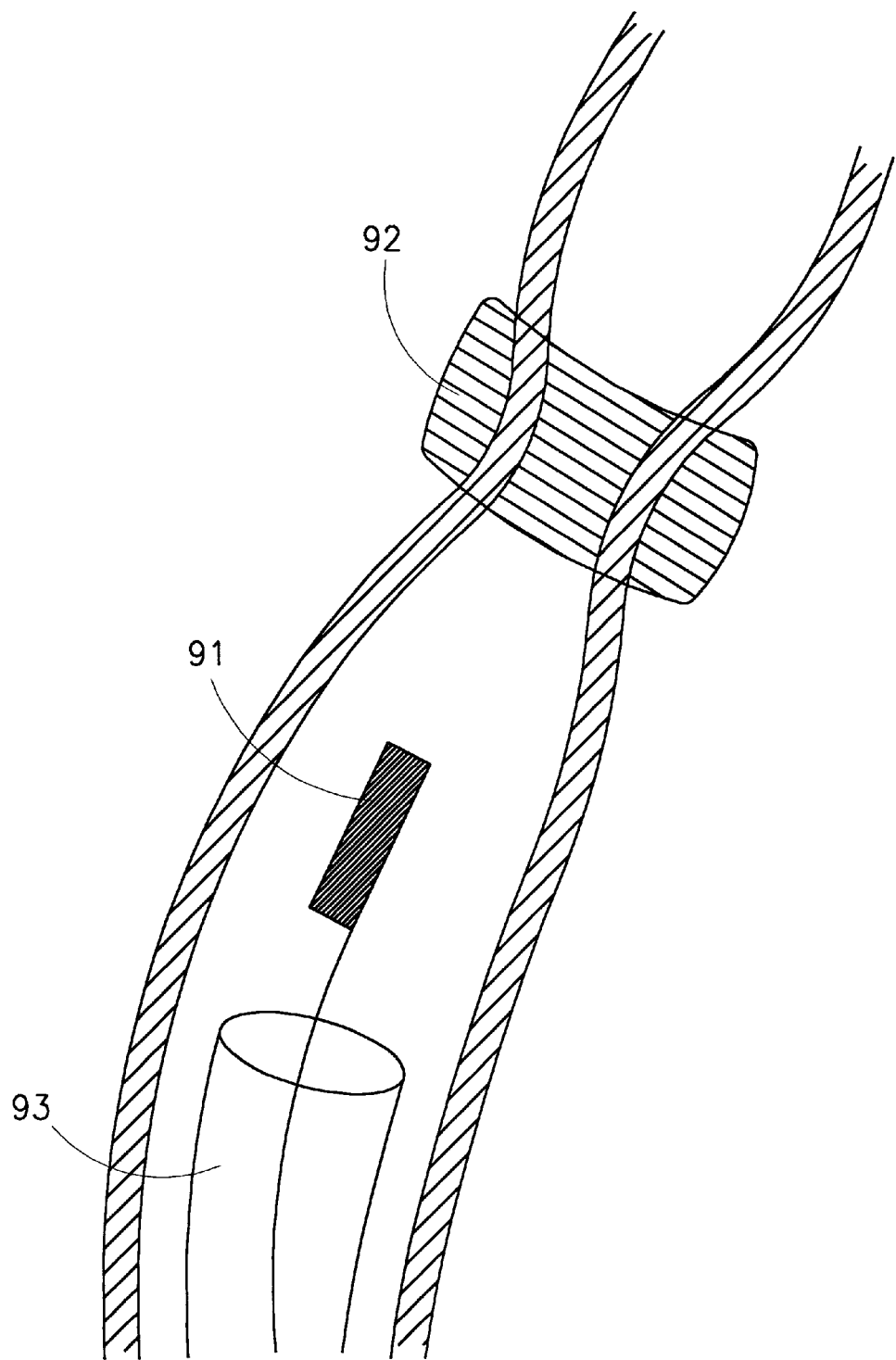
FIG. 10 is isometric description of a pig carotid exposed and partially occluded in an in-vivo study, including the PSG unit and the single pressure sensor.
Figure 25:
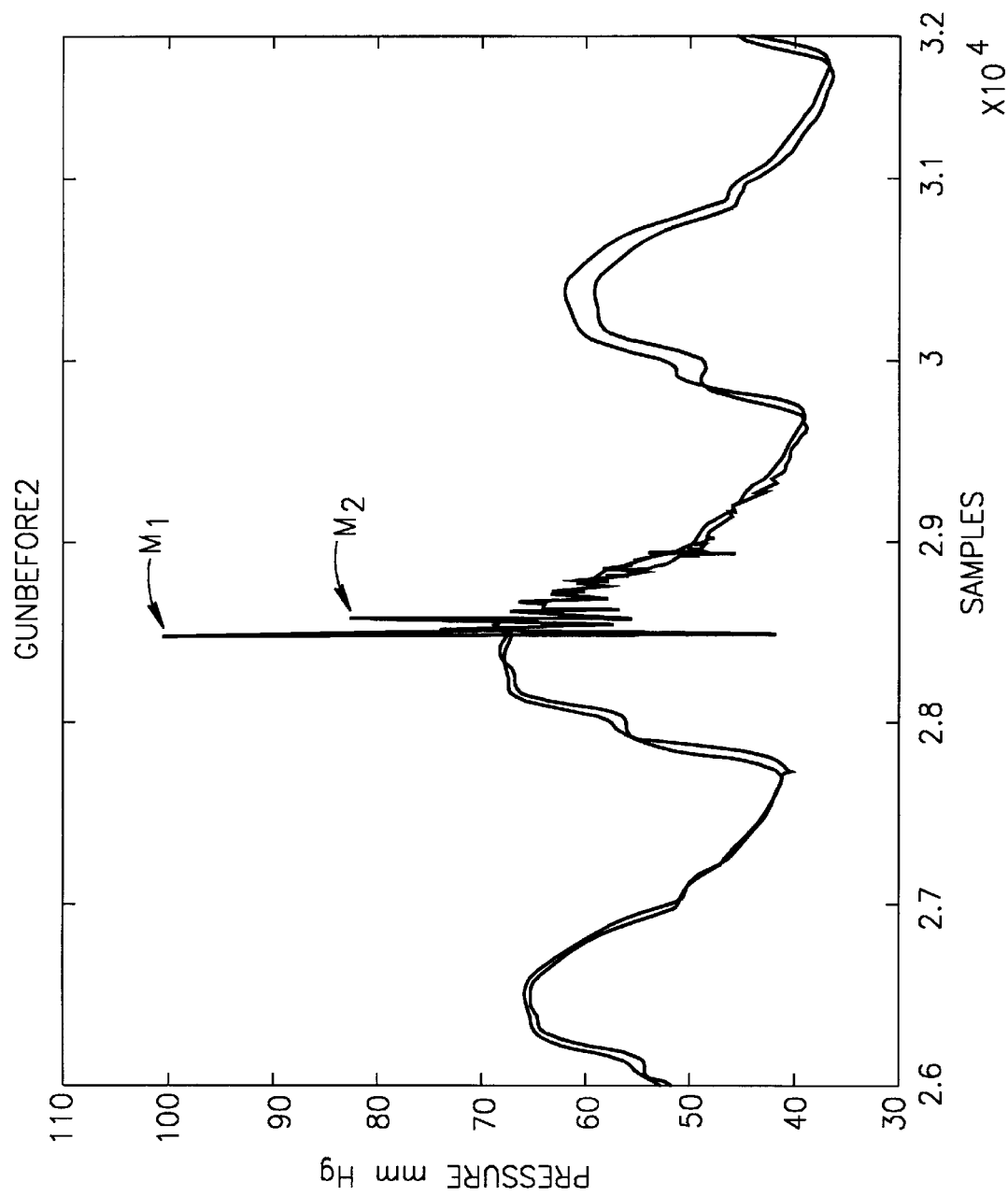
FIG. 25 is a graph describing the pressure as measured in an in-vivo study, in an occluded vessel, after application of an excitation pressure, in a system as described in FIG. 10.

Reference is now made to FIG. 10. In-vivo experiment was performed on a pig carotid using a single pressure sensor 91 inserted into the vessel via a standard 8F catheter 93. An artificial occlusion 92 was applied about 5 cm distal to the pressure sensor 91, created by an external occluder balloon (Vascular Occluder, IN VIVO METRIC, California, U.S.A.) causing blood vessel lumen diameter reduction to about ⅔ of the original diameter (about 50% lumen area reduction)—estimation has been performed based on angiographics. An artificial flow/pressure signal has been introduced into the catheter using the syringe acted by a pistol hammer mechanism described in FIG. 8. An unknown input pressure signal was applied. Pressure versus time data measured by the pressure sensor 91 are shown in FIGS. 25 and 26.

Figure 26:
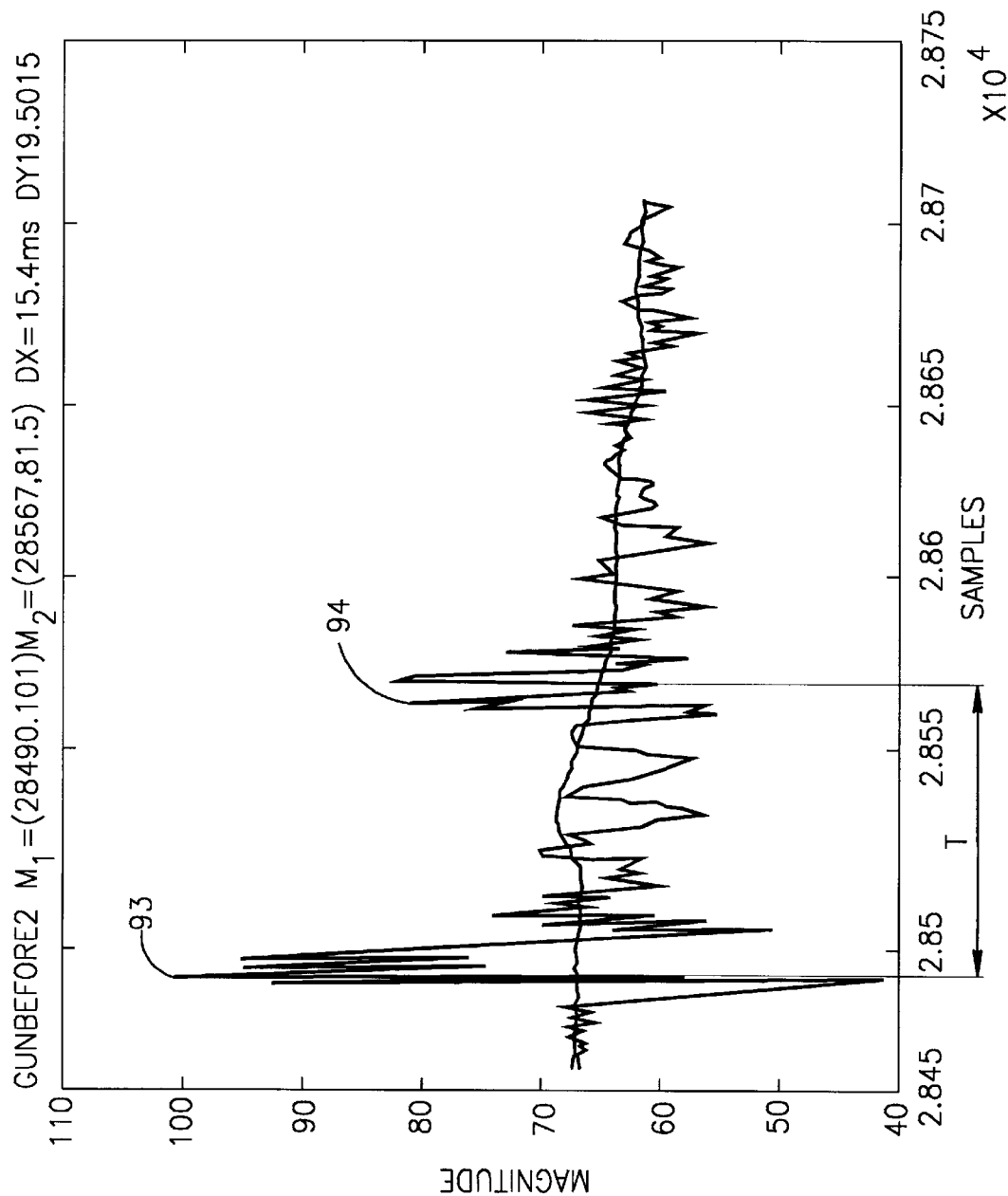
FIG. 26 is a closed view of the signal presented in FIG. 25.
Figure 27:
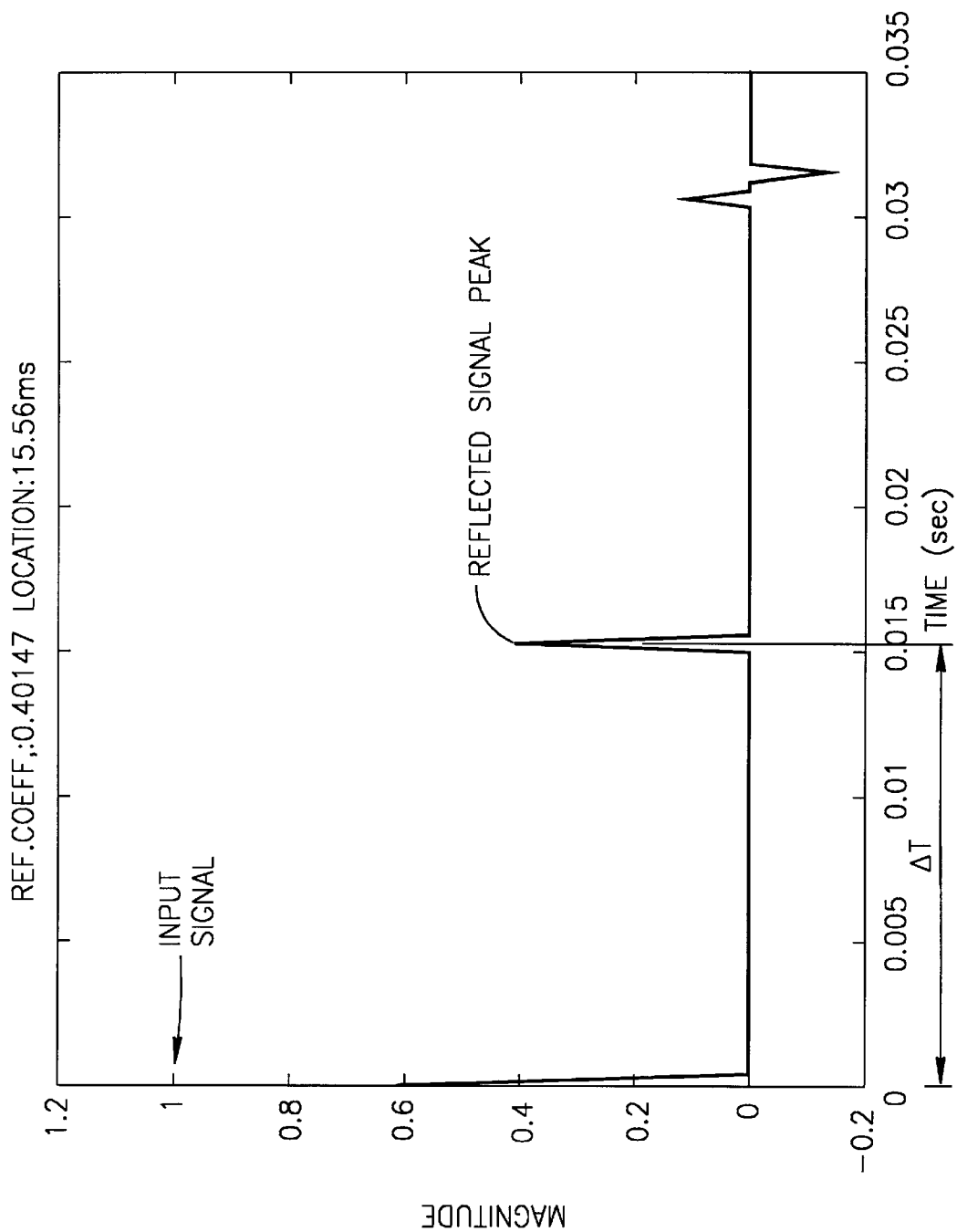
FIG. 27 is the result of Procedure 2 applied to the data presented in FIGS. 25 and 26, illustrating the separation into two peaks, for the forward and backward signals.

The two peaks shown in FIG. 26 are the pressure input signal 93, and the reflected pressure signal 94. The data were processed by Procedure 2. FIG. 27 shows the result of the analysis: two major peaks representing the timing and amplitude of the forward pulse and the reflected pulse. The distance between the two peaks in msec (T) is measured from the graph. The velocity of the pressure wave was found –5.5 m/sec. The distance of the stenosis from the pressure sensor is calculated using the velocity and time interval: 0.016×5.6=0.09. The distance to stenosis is therefore 0.09/2=4.5 cm, similar to the distance which was measured angiographically). The calculated reflection coefficient was found to be 0.4. This correlates well with the calculation based on $R_f=(Ao-As)/(Ao+As)$ presented hereinabove: $Ao=\pi 16$ mm$^2$, $As=\pi 6.25$ mm$^2$ resulting in a reflection coefficient of 0.44.

METHOD NO. 2: Single Pressure Sensor—Long Range Stenosis

Data Acquisition

The method is described in FIG. 9. A single pressure sensor 4 is inserted into the blood vessel of interest 30 and positioned at point A, upstream the stenosis. The distance between the sensor and the stenosis result in a separation of the exciting pressure wave (forward wave) and the reflected wave (backward wave). Pressure pulse is applied by the pulse generator 5 and data of pressure versus time Pa(t), at point A, are obtained.

Data Analysis

The system uses the two pressure function procedure (Procedure 1) to detect the existence and location of stenosis, aneurysm or vascular bed. No prior knowledge of the exciting signal is required. The procedure is taking advantage of the inherent separation of the forward and backward components of the signal. The procedure is modified to recognize the input signal, w(n), from the first part of the output signal, and apply the Procedure 1 to the second part of the signals, s(n). The system uses the method described in FIG. 17 to estimate the severity of stenosis or aneurysm.

Input Data Required for Using the Procedure

1. Pressure versus time function Pa(t), measured by the single sensor 4.
2. Pressure wave velocity. The velocity was calculated using Procedure 4 or assumed to be known from previous test data.

Output Results
1. Location of stenosis, aneurysm or vascular bed.
2. Stenosis or aneurysm severity.

In-Vitro Experimental Results

Figure 28A:
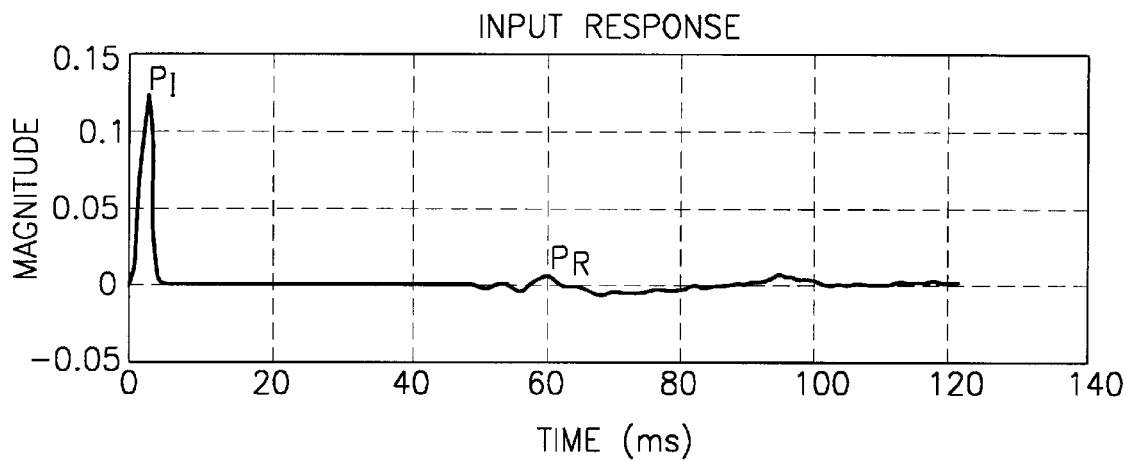
FIG. 28 is the result of Procedure 1 applied in a long range case as presented in Method no. 2. The upper signal is the analysis result of the measured signal presented in the lower figure.
Figure 28B:
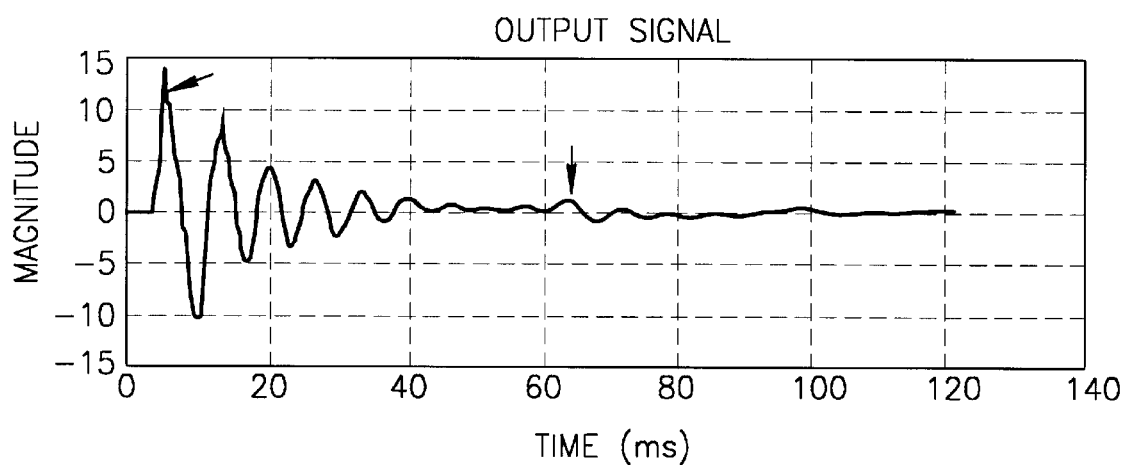

Data were acquired on the in-vitro system described in FIGS. 5–7, with a single pressure sensor, 24a, within. FIG. 28 illustrates the application of the Procedure 2 on an in-vitro pressure data. The lower part of FIG. 28 presents the pressure versus time as measured by the pressure sensor, Pa(t), located at A. The upper part of FIG. 28 presents the result of the Procedure 1, where the 2 peaks, of the input pressure wave ($P_I$), and the reflected wave ($P_R$) can be clearly observed. The time interval between the two peaks is calculated from FIG. 28 to be 56 msec. Knowing the velocity of the pressure wave, 14 m/sec, allows calculating the stenosis location: 0.056×14=0.392 m. This is a perfect match to the 40 cm distance between the transducer and the stenosis.

METHOD NO. 3: Single Pressure Sensor—Known Input Signal

Data Acquisition

The method is described in FIG. 9. A single pressure sensor is inserted into the blood vessel of interest 30 and positioned at point A. Pressure pulse is applied by the pulse generator 5 and data of pressure versus time Pa(t), at point A, are obtained. The applied pressure signal is controlled and known from the pulse generator 5. The transfer function of the catheter is assumed to be known. Therefore the input pressure signal entering the blood vessel is known.

Data Analysis

The system uses the dual pressure function procedure (Procedure 1) to detect the existence and location of stenosis, aneurysm or vascular bed. The system uses the method described in FIG. 17 to estimate the severity of stenosis or aneurysm.

One could refer to the in-vitro example discussed in Method 6, and presented in FIG. 19, as a demonstration of the actual method, where the upstream pressure signal is considered as a known input.

Input Data Required for Using the Procedure
1. Pressure versus time function Pa(t), measured by the sensor 4.
2. Pressure wave velocity. The velocity is assumed to be known from previous test data or calculated using Procedure 4.
3. Catheter transfer function. The pressure versus time transfer function is assumed to be known from previous test results.
4. Exciting signal (forward pressure wave). The signal magnitude, duration and shape are controlled and known by the pressure generator 5.

Output Results
1. Location of stenosis, aneurysm or vascular bed.
2. Stenosis or aneurysm severity.

METHOD NO. 4: Single Pressure Sensor—Two Measuring Sites

Data Acquisition

Figure 18:
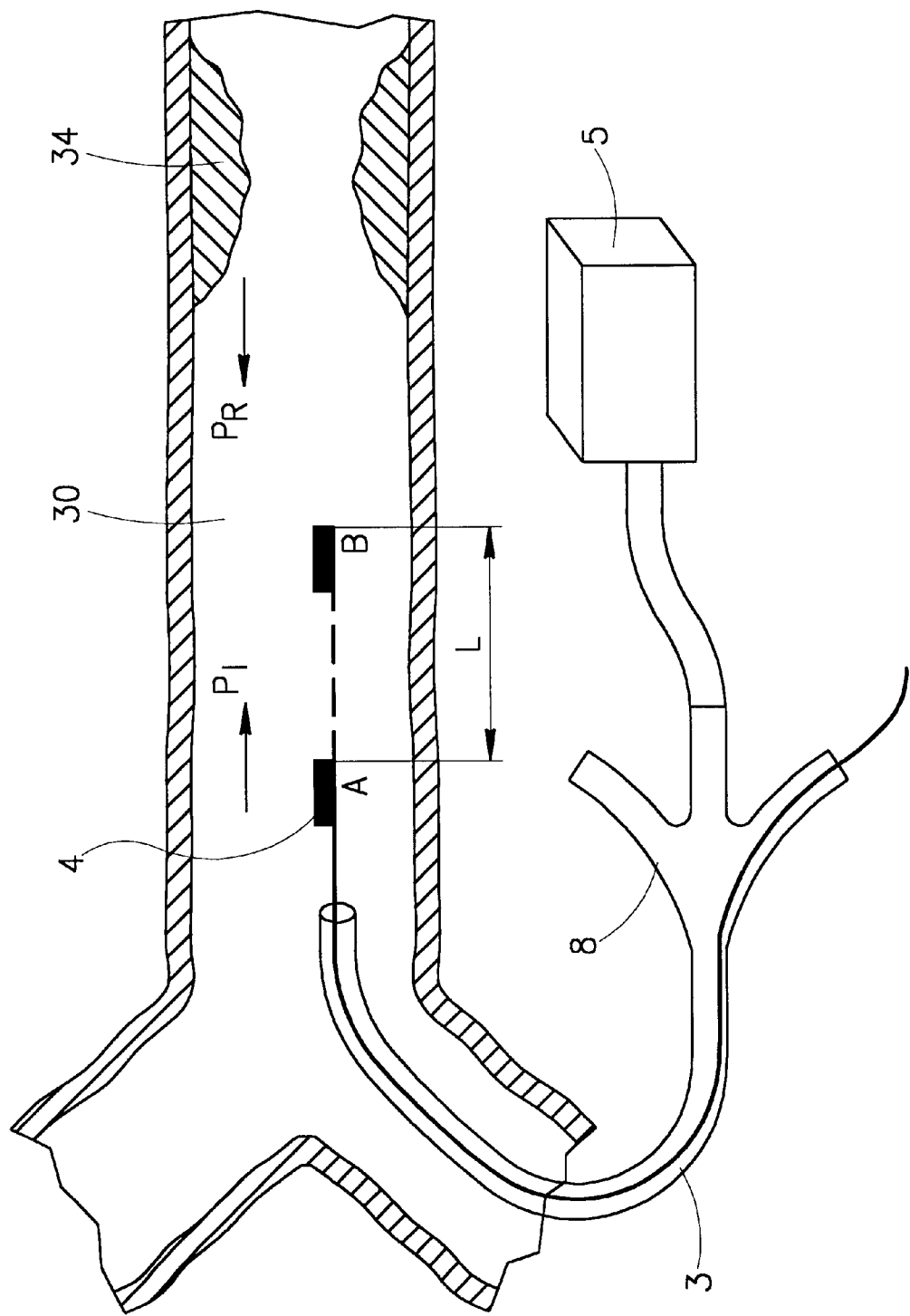
FIG. 18 is an isometric description of the setup used in Method 4 including the PSG unit, a pressure sensor measuring at two points A and B, and a catheter within a stenosed blood vessel.
Figure 19A:
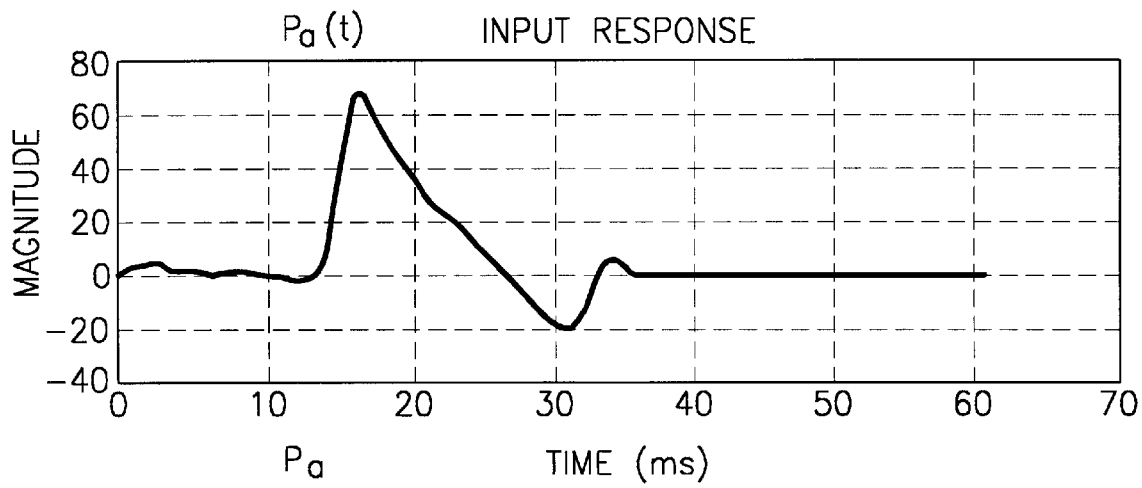
FIGS. 19(a)–19(e) present the result of the analysis which separate the forward and backward signals.
Figure 19B:
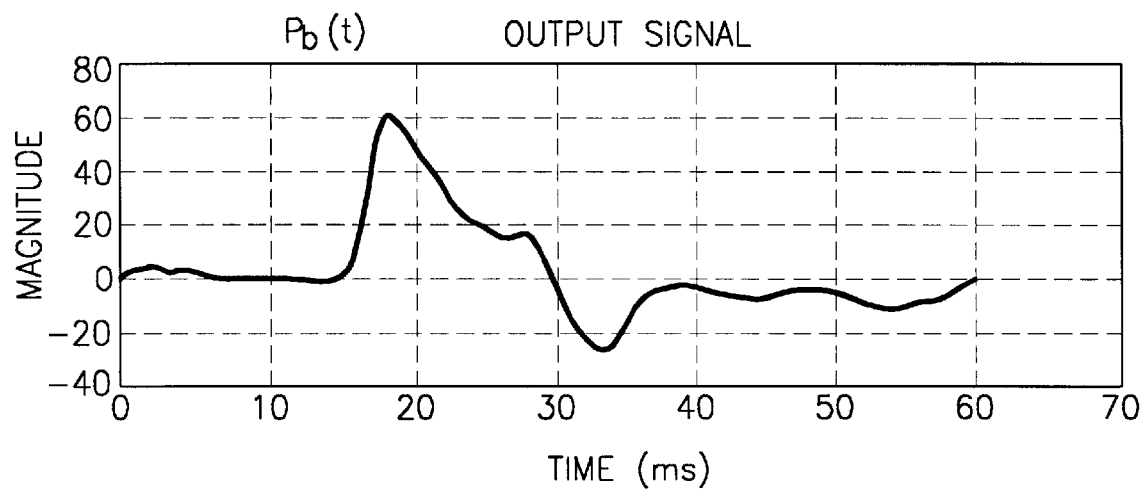
Figure 19C:
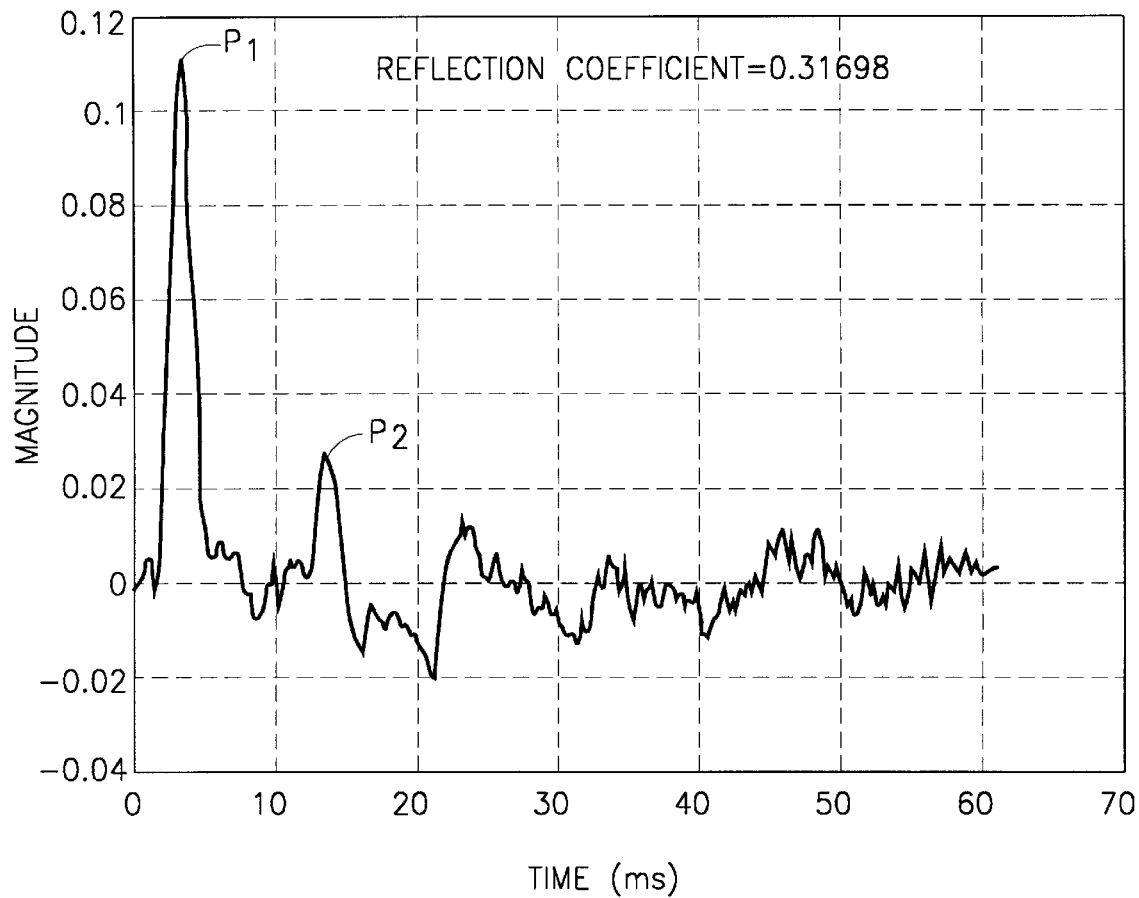
Figure 19D:
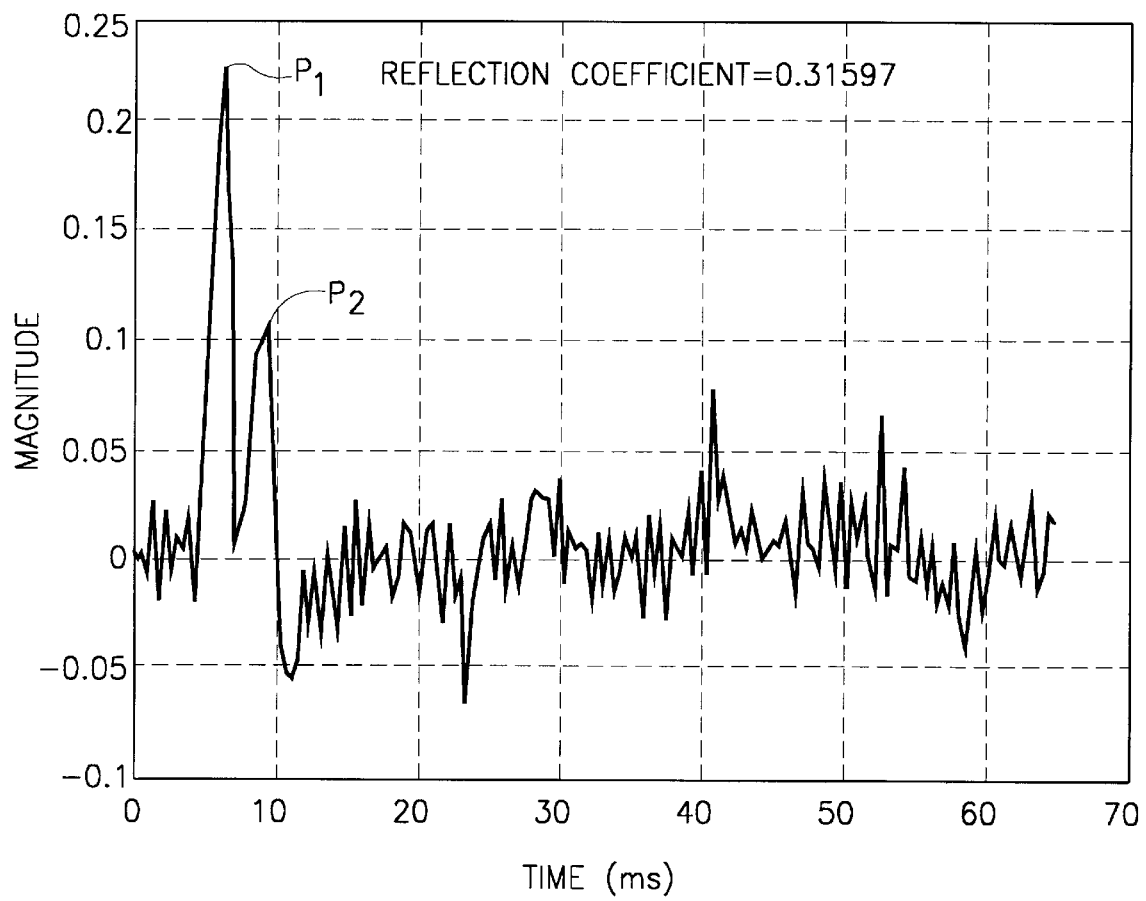
Figure 19E:
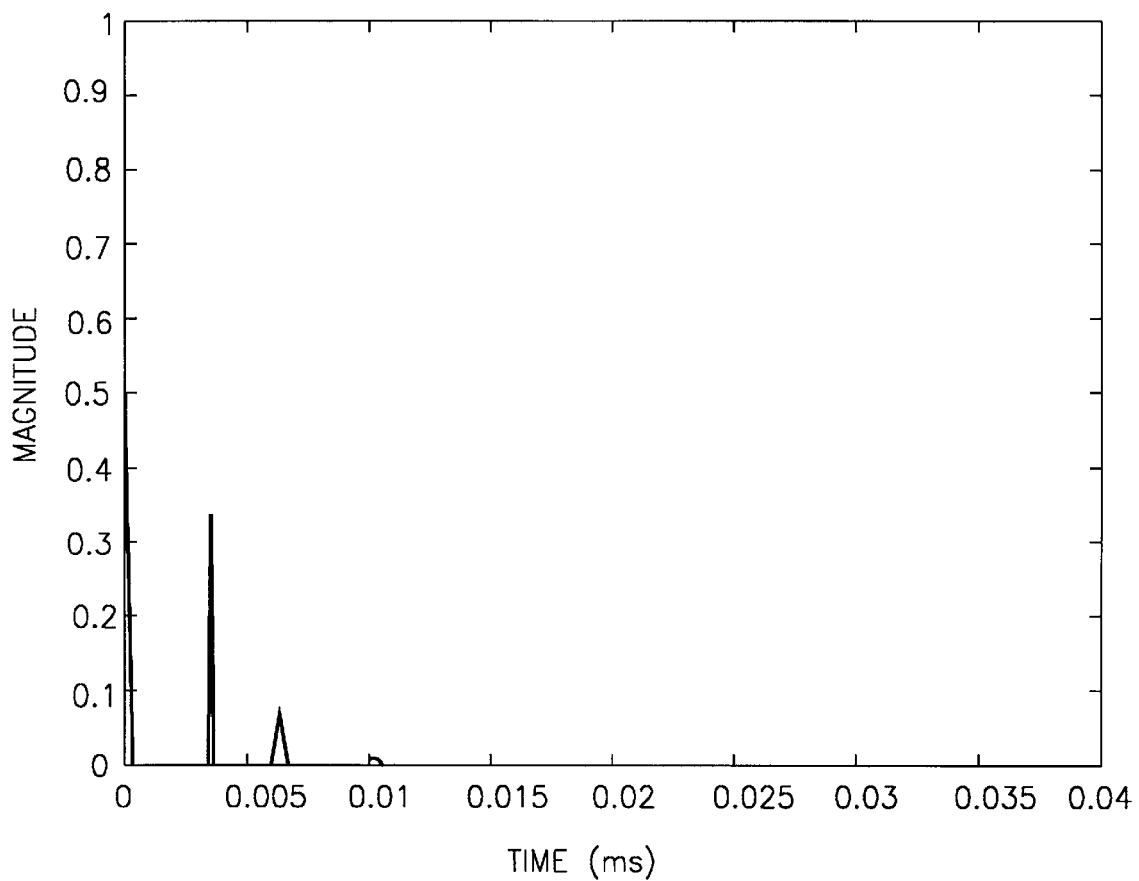

The method is described in FIG. 18. A single pressure sensor is inserted into the blood vessel of interest and positioned at point A. Pressure pulse is applied by the pulse generator 5 and data of pressure versus time Pa(t), at point A, are obtained. The pressure sensor is now moved downstream, by a known distance L and positioned at point B. The pressure generator 5 generates a similar pressure pulse, and data of pressure versus time, Pb(t), are obtained.

Data Analysis

The system uses the dual pressure function procedure (Procedure 1) described above to detect the existence and location of stenosis, aneurysm or vascular bed. The system uses the method described in FIG. 17 to estimate the severity of stenosis or aneurysm. One could refer to the in-vitro example discussed in Method 6, and presented in FIG. 19, as a demonstration of the actual method, where the upstream pressure signal is acquired by the same pressure sensor location in A and the downstream signal is acquired by the same pressure sensor moved to B.

Input Data Required for Using the Procedure
1. Pressure versus time measured at location A—Pa(t).
2. Pressure versus time measured at location B—Pb(t).
3. Pressure wave velocity. The velocity is assumed to be known from previous test data, or evaluated using the single pressure PWV procedure.
4. Input signal (forward pressure wave). The signal magnitude, duration and shape are controlled and known by the pressure generator.

Output Results
1. Location of stenosis, aneurysm or vascular bed.
2. Stenosis or aneurysm severity.

METHOD NO.5: Two-Pressure Sensors—Visual Method

Figure 13:
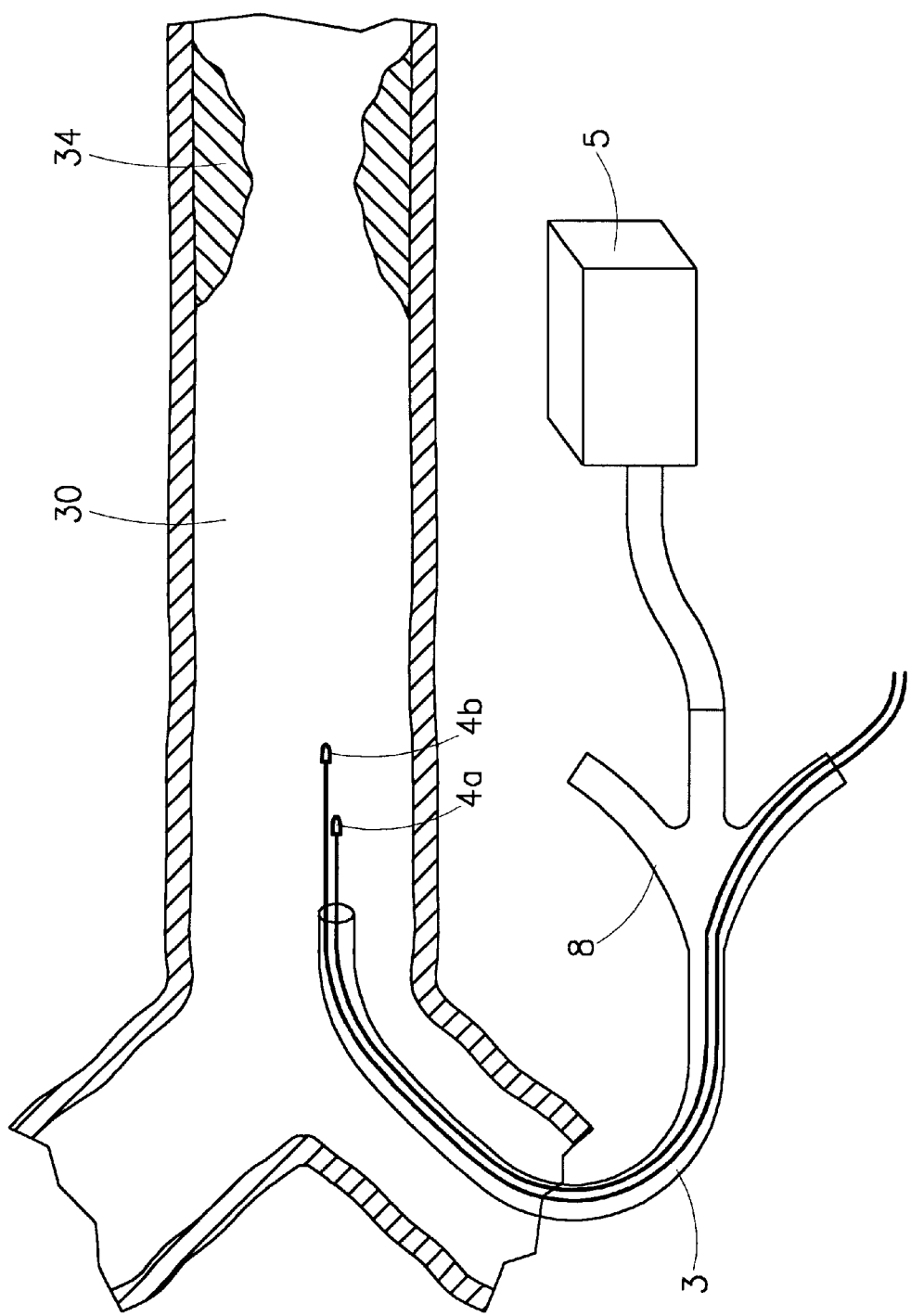
FIG. 13 is an isometric description of the setup used in Method 5 including the PSG unit, the two pressure sensors and the catheter within a stenosed blood vessel.

Reference is now made to FIG. 11 and 13. Two pressure sensors 4a and 4b are inserted into the blood vessel 30 of interest via a standard connector 8 connected to a catheter 3. In another embodiment, the pressure sensors 4a and 4b may be mounted on a mutual wire or catheter (e.g. Millar 2.5F dual sensor model SOPC-721, Millar Instruments Inc., Texas, U.S.A.). In another embodiment, the pressure sensor 4a may be a fluid filled manometer sensor connected to the catheter 3 via the connector 8. The pulse generator 5 applies a pressure pulse. Data of pressure versus time are obtained from pressure sensors 4aand 4b. FIG. 10 describes a blood vessel without stenosis. FIG. 13 describes a blood vessel with a downstream stenosis. PWV may be either calculated using Procedure 3 or known from prior art.

Data Analysis—In-Vitro Experimental Results

Figure 12:
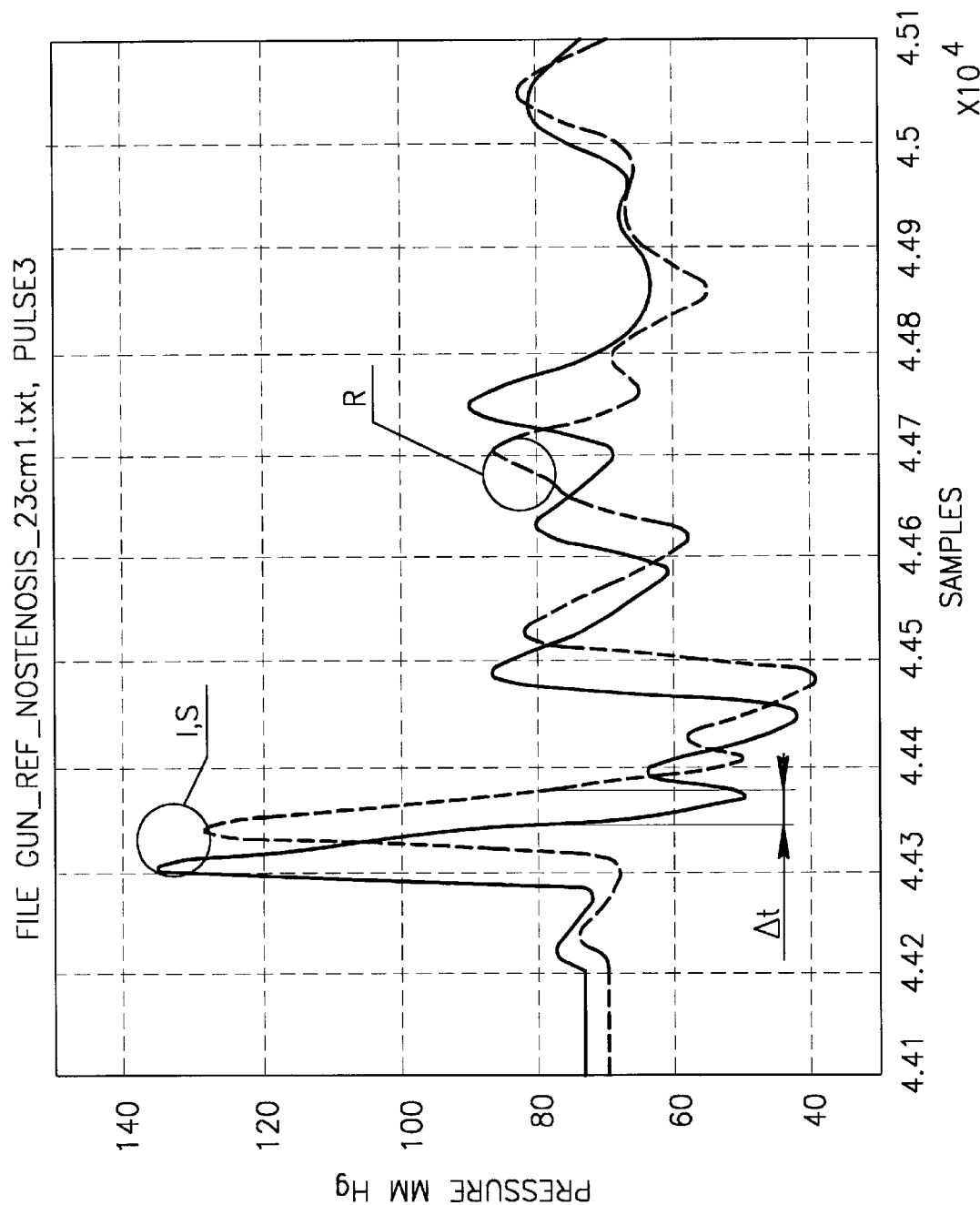
FIG. 12 is a graph describing pressure versus time (no. of samples) in a two pressure sensors measurement in-vitro setup as shown in FIG. 11.
Figure 14:
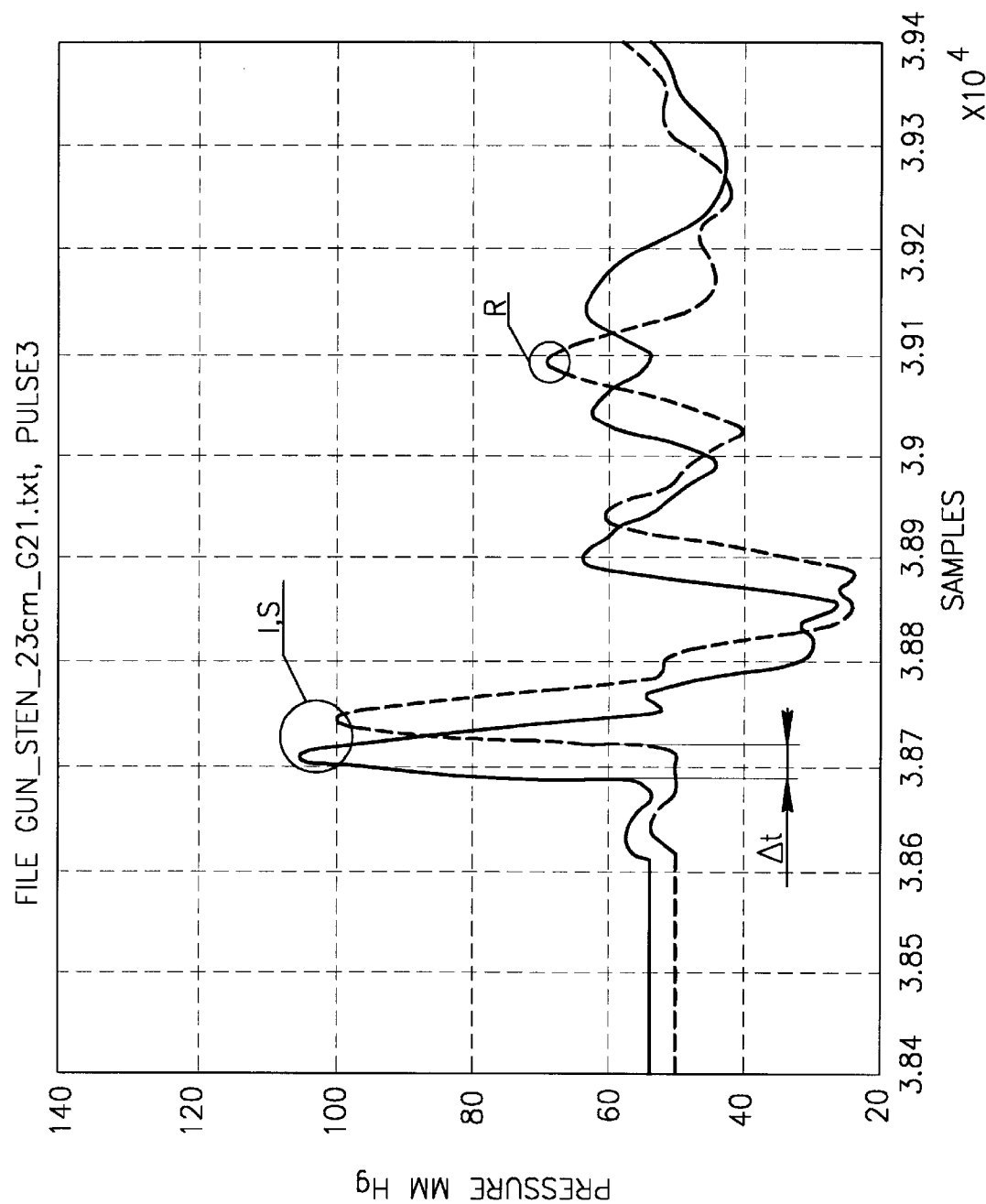
FIG. 14 is a graph describing pressure versus time (no. of samples) in a two pressure sensors measurement in-vitro setup as shown in FIG. 13.

Reference is now made to FIG. 12 and 14. FIG. 12 describes pressure changes versus time (number of samples), sampled at 5000 samples/sec. Data were obtained on the in vitro system described in FIGS. 5–7. The system does not include stenosis inside the vessel, however far reflections occur from the system bath 44 right edge. FIG. 12 serves as a reference data for cases where stenosis does exist in a blood vessel. The vertical axis indicates the pressure values in units of mmHg. The horizontal axis indicated the number of samples. The two curves in FIG. 12 indicate the pressure value at two different points along the vessel, at the location of the two pressure sensors 24a and 24b. The dashed line is used for pressure measured by the sensor 24A and dotted line for the pressure measured by the sensor 24B.

FIG. 14 describes the pressure changes versus time as explained for FIG. 12. Data acquisition was preformed using the system described in FIGS. 4–6, with the presence of a stenosis, as described in FIG. 13. The pressure pulse is similar to the pulse generated for the case described in FIG. 12 (without stenosis). When a stenosis exist in a blood vessel, a visible and detectable change in the pattern of the pressure waves can be identified. This change is caused by the reflection of the pressure wave from the occluded site. The use of two transducers allows accurate identification of the reflection point. The pressure wave created by the pressure generator 5 advances and reaches first the upstream pressure sensor 24A and later the downstream sensor 24B, so that a time delay, Dt, exist between the signal measured by the pressure sensor 24a and the signal measured by the pressure signal 24b. The pressure wave measured by the upstream sensor (24a) is ahead of the pressure measured by the downstream sensor (24b). In FIG. 13, the dashed line is used for pressure measured by sensor 24A and dotted line for sensor 24B.

When a stenosis exist the reflected wave reaches first the downstream sensor 24B and later the upstream sensor 24A. This causes a change in the order of propagation of the two waves, so that the pressure wave measured by the downstream sensor 24b is now ahead of the other pressure wave 24a. The change in the order of the propagating waves is an indication for the existence of reflection caused by a stenosis. The point along the time axis, where the change in order of the propagating waves occurs, was used to determine the location of the stenosis.

Figure 15:
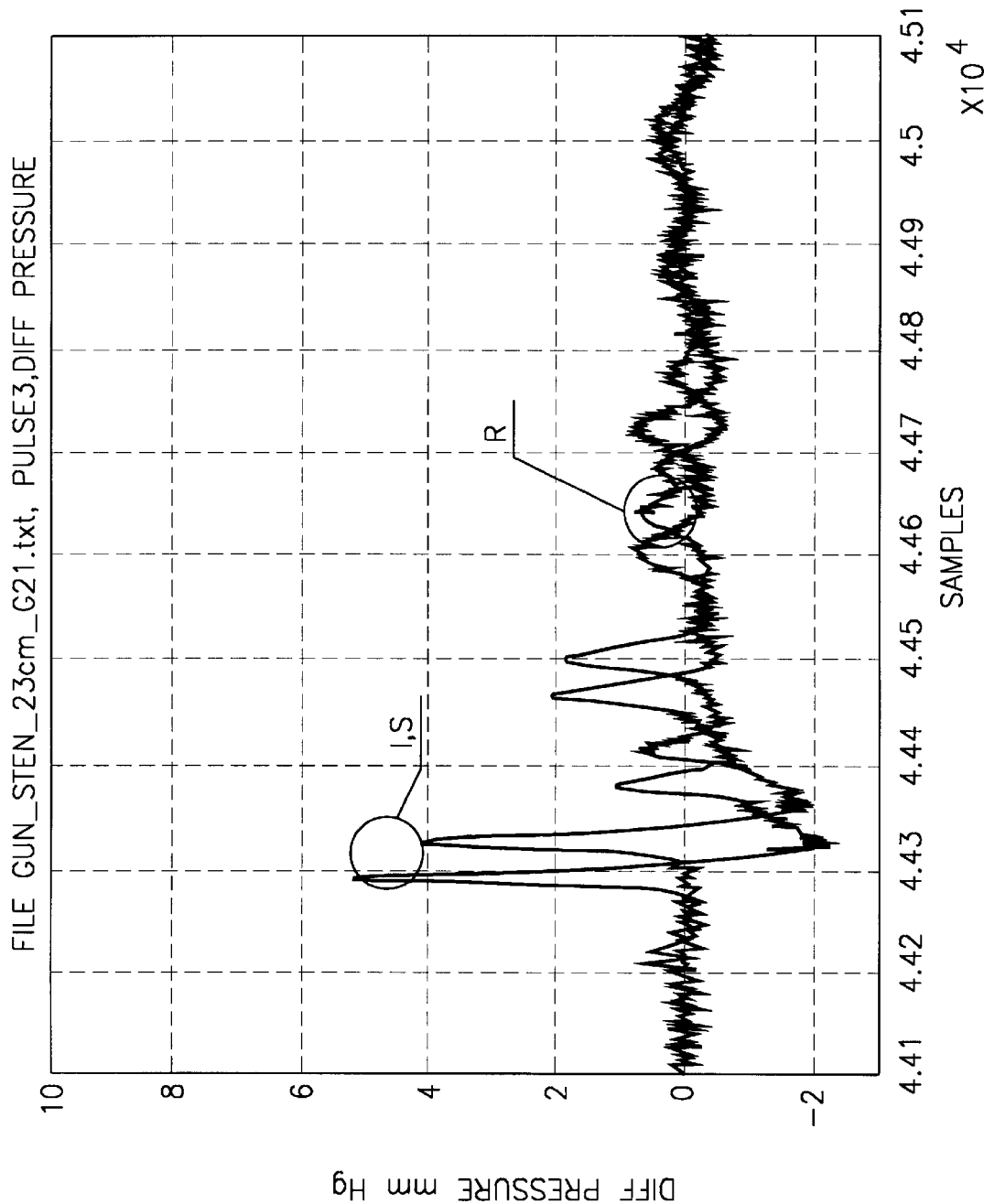
FIG. 15 is a graph describing the pressure time derivative versus time (number of samples) as calculated from the data described in FIG. 12.
Figure 16:
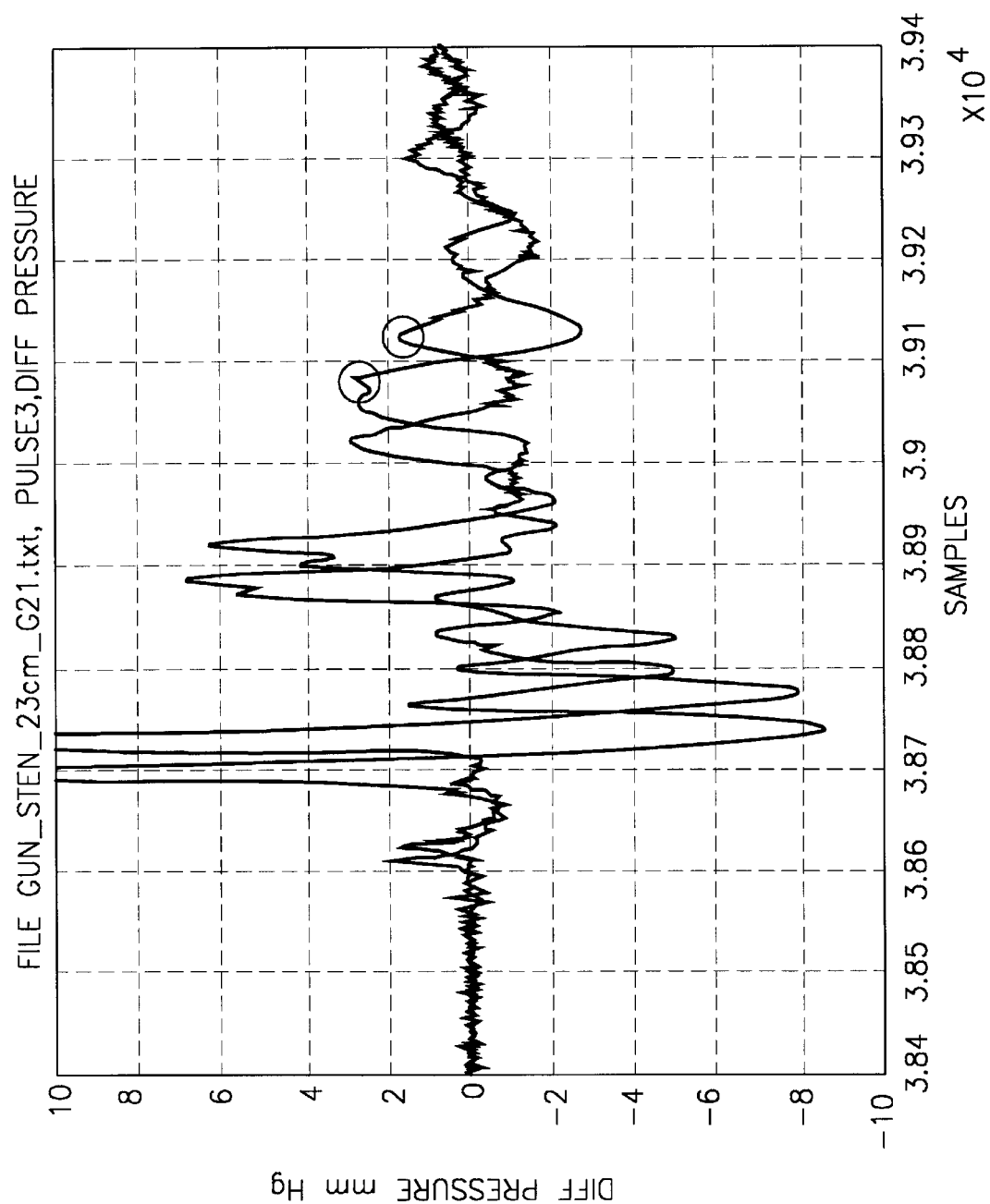
FIG. 16 is a graph describing the pressure time derivative versus time (number of samples) as calculated from the data described in FIG. 14.

Reference is now made to FIG. 15 and 16. The vertical axis represents the pressure time derivative (dp/dt) as calculated from the data of FIG. 12 and 14. The use of pressure time derivative instead of the pressure may simplify the identification of the reflection point. FIG. 15 presents the pressure time derivative versus time as measured by sensors 24a and 24b in the case where the system does not include stenosis. FIG. 16 presents the pressure time derivative versus time obtained from the system with stenosis.

Output Results

1. Location of stenosis, aneurysm or vascular bed.
2. Pressure wave velocity.

METHOD NO.6: Two-Pressure Sensors—Analytical Method

Reference is now made to FIG. 11. Two pressure sensors 4a and 4b are inserted into the blood vessel 30 of interest via a standard connector 8 connected to a catheter 3. In another embodiment, the pressure sensors 4a and 4b may be mounted on a mutual wire or catheter (e.g. Millar 2.5F dual sensor model SPC-721, Millar Instruments Inc., Texas, U.S.A.). In another embodiment, the pressure sensor 4a may be a fluid filled manometer sensor connected to the catheter 3 via the connector 8. The pulse generator 5 applies a pressure pulse. Data of pressure versus time are obtained from pressure sensors 4a and 4b.

Data Analysis

The system uses the dual pressure function procedure (Procedure 1) described above, to detect the existence and location of stenosis, aneurysm or vascular bed. The system uses the method described in FIG. 17 to estimate the severity of stenosis or aneurysm.

Output Results

1. Location of stenosis, aneurysm or vascular bed.
2. Stenosis or aneurysm severity.
3. Pressure wave velocity.

In-Vitro Experimental Results

FIG. 19 illustrates the application of the procedure on two pressure in-vitro data, where one pressure transducer was 12 cm and a second pressure transducer was located 7 cm upstream the stenosis. FIG. 19a presents the pressure versus time as measured by the upstream sensor, Pa(t), located at A, 12 cm from the stenosis. FIG. 19b presents the pressure as measured by the downstream sensor, Pb(t), located at B, 7 cm from the stenosis. The result of the Procedure 1 is presented in FIG. 19c, where the 2 peaks, of the input pressure wave (PI), and the reflected wave (PR) can be clearly observed. The time interval between the two peaks is calculated from the graph—10 msec. Knowing the velocity of the pressure wave, 14 m/sec, allows calculating the stenosis location: 0.01×14/2=0.07 m, which is a perfect match to the experiment setup. Stenosis severity or reflection coefficient was calculated according to the area ratio, as explained above. The calculated coefficient is 0.317. A third pressure sensor was located 2 cm from stenosis. The same procedure was applied again and results are presented in FIG. 19d. Calculated distance using the time difference between the peaks (3 msec) is 2.1 cm, and the reflection coefficient is 0.316. The same reflection coefficient was expected and calculated for both transducers at 2 cm and 7 cm, in reference to the same stenosis. Verification for the value of the expected reflection coefficient is offered by the equation $R_f=(Ao-As)/(Ao+As)$ presented hereinabove: $Ao=16$ mm$^2$, $As=9$ mm$^2$ then $R_F=7/25=0.28$. Moreover, applying the Procedure 2 on the same data resulted in a reflection coefficient of 0.34, and the same calculated distance, as presented in FIG. 19e.

METHOD NO.7: Flow Rate Measurement

Data Acquisition

The system used for data acquisition is described in FIG. 9. A flow rate sensor (replacing the pressure transducer 4) is inserted into the blood vessel of interest 30 and positioned at point A. Pressure pulse is applied by the pulse generator 5 and data of flow rate versus time Qa(t) at point A, are obtained.

Data Analysis

Figure 20:
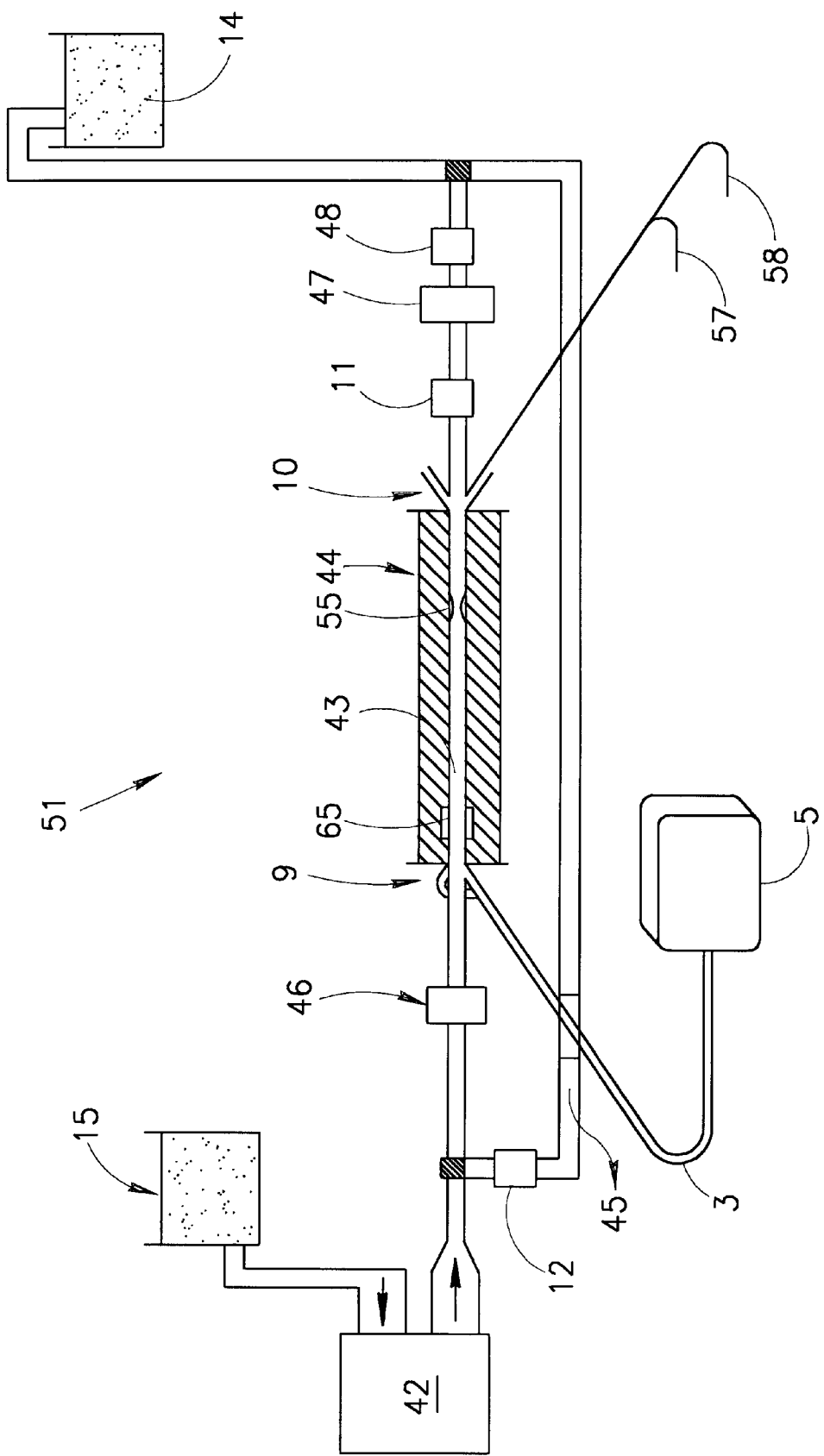
FIG. 20 is schematic cross section illustrating the in-vitro recirculating system 51 of system 41 of FIG. 5, with the addition of an ultrasonic flowmeter 65 and a stenosis 55.
Figure 21:
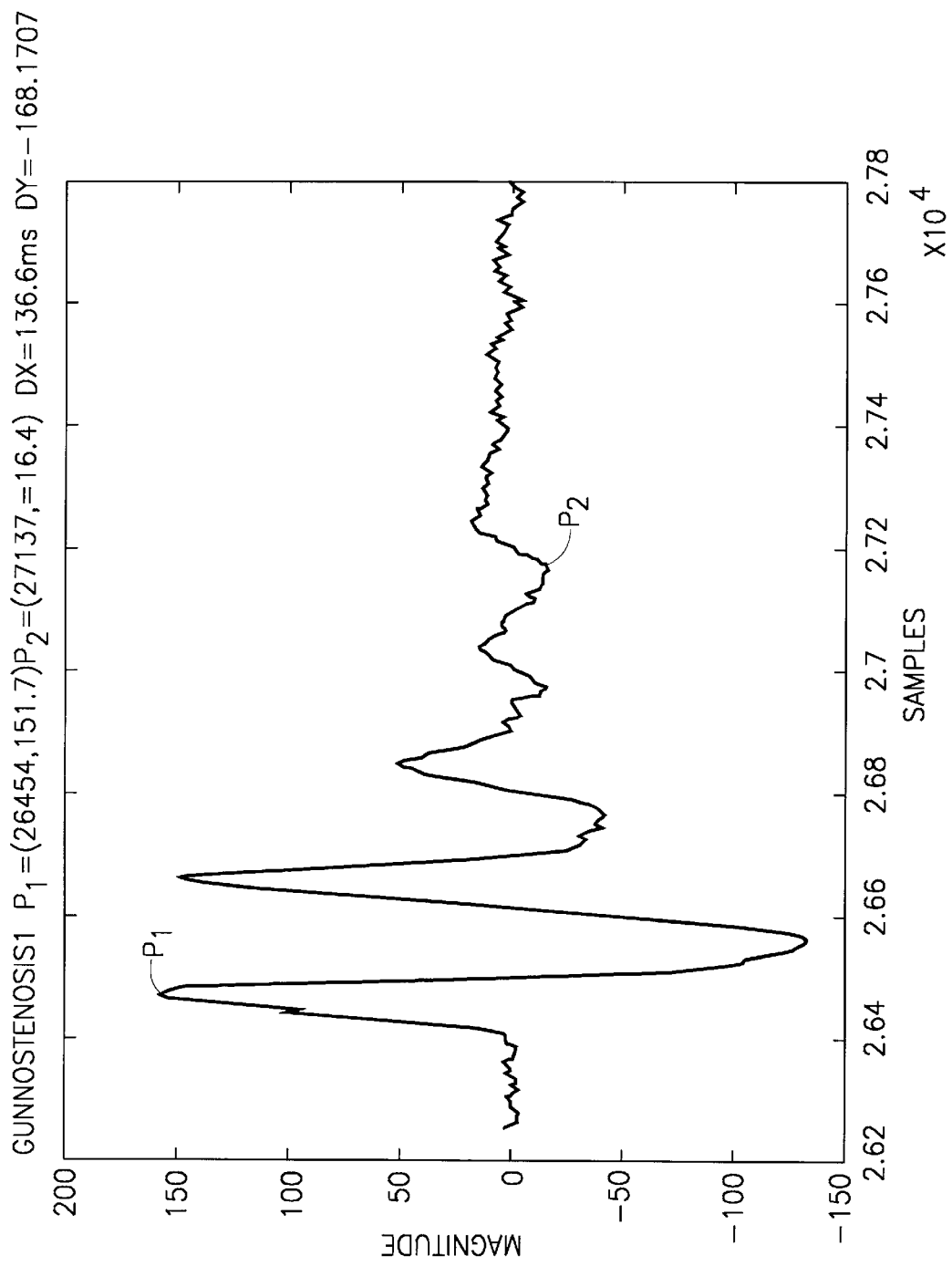
FIG. 21 is a graph describing the flow (ml/min) versus time (no. of samples) measured within the in-vitro system 51 of FIG. 6, and with a stenosis at a distance of 95 cm.
Figure 22:
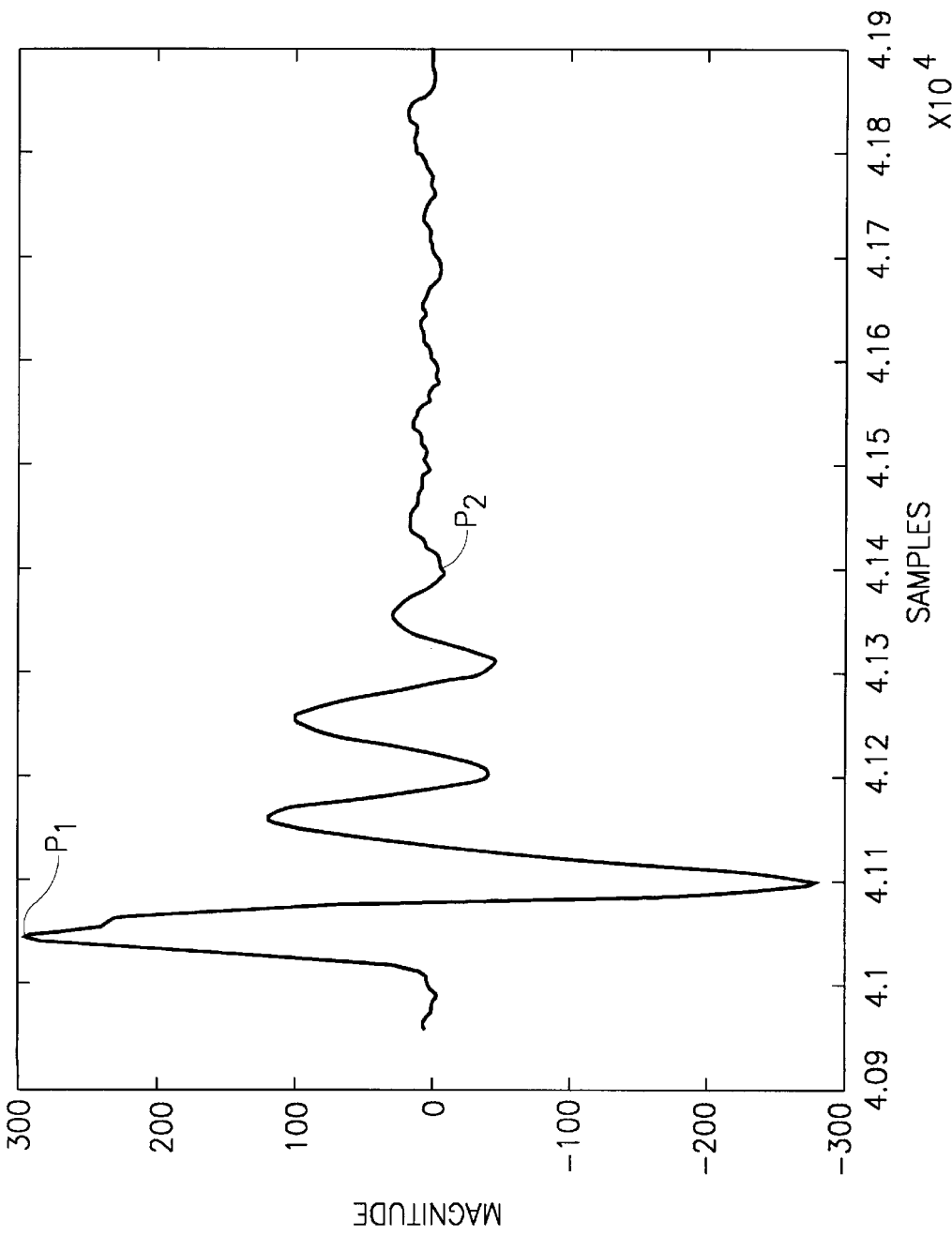
FIG. 22 is a graph describing the flow (ml/min) versus time (no. of samples) measured within the in-vitro system 51 of FIG. 6, and with a stenosis at a distance of 50 cm.
Figure 23:
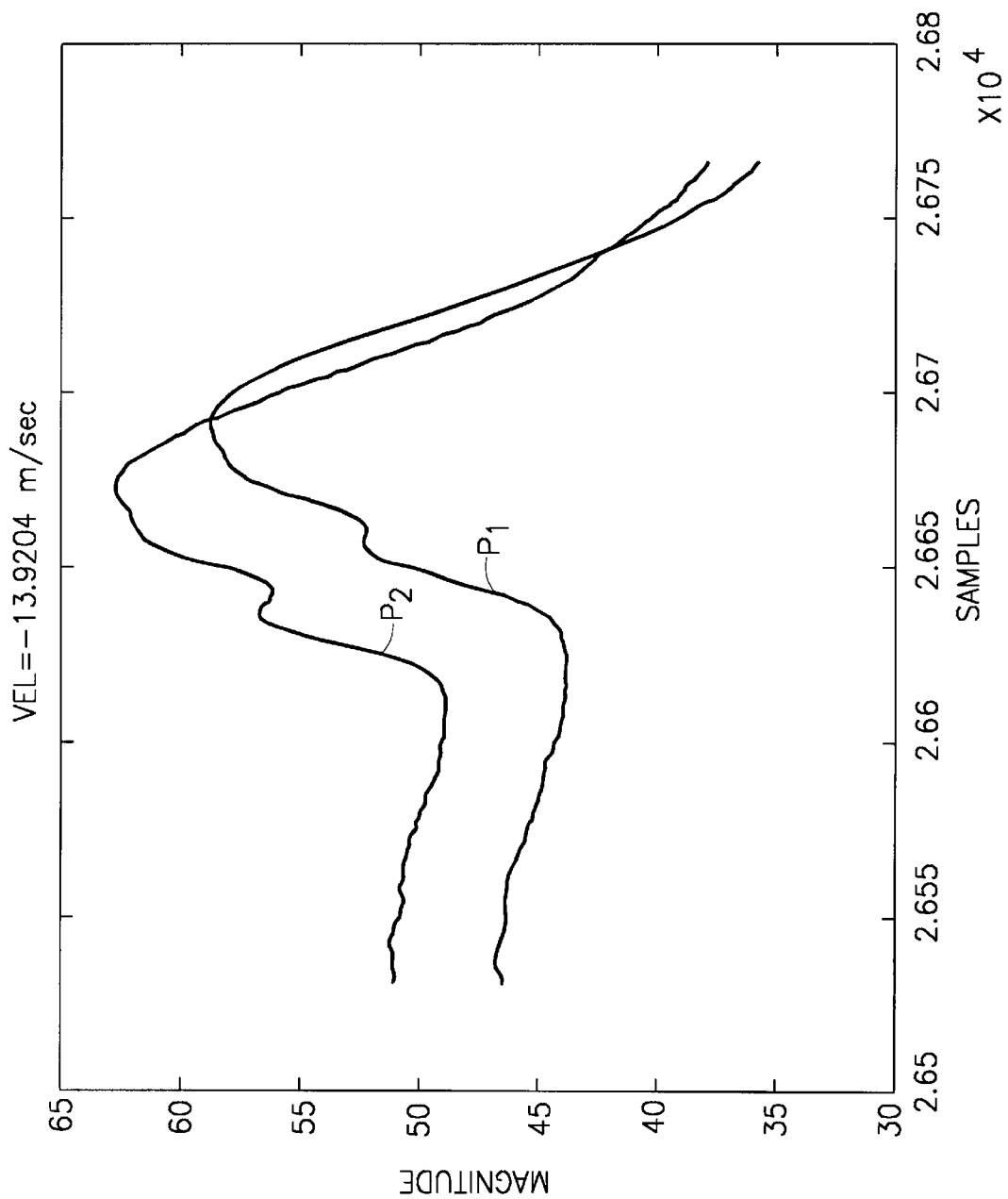
FIG. 23 is a graph of two pressure measurements, demonstrating the calculation of pressure wave velocity using Procedure 3.

Reference is now made to FIG. 21–22, presenting data acquired on the in-vitro system described in FIGS. 4–7 and modified to include an ultrasonic flowmeter (model T206, Transonic Systems Inc., New York, U.S.A.) and a stenosis 55, as shown in FIG. 20. FIGS. 21 and 22 present the flow rate changes versus time (number of samples). A sharp increase in the flow rate when pressure excitation is applied by the pulse generator 5, followed by a gradual decay. This response is similar to the pressure signal. Therefore, all methods of analysis described for the pressure signals are applicable. Visual inspection of FIGS. 21, reveals a change in the signal development marked P2, corresponding to the reflection from a stenosis at 95 cm distance. Using the observed time delay of 683 samples (equivalent to 136.6 msec), we get 0.1366×13.9/2=95 cm. FIG. 22, reveals a change in the signal development marked P2, corresponding to the reflection from a stenosis at 50 cm distance. Using the observed time delay of 74.6 msec, we get 0.0746×13.9/2=52 cm. These calculations are based on a pressure wave velocity, 13.9 m/sec, deduced from pressure data acquired with two pressure transducers located 5.5 cm apart, using Procedure 3, and shown in FIG. 23.

The change in the signal, designated P2, presented in FIGS. 21 and 22 differs from the change in the pressure signals observed above. The different reflection appearance originates from the fact that a forward flow is reflected as a refraction wave, as a negative flow, therefore the superposition of the forward and backward flows result in a decrease in amplitude ('a valley') and not an increase as observed with the pressure signals.

Figure 24:
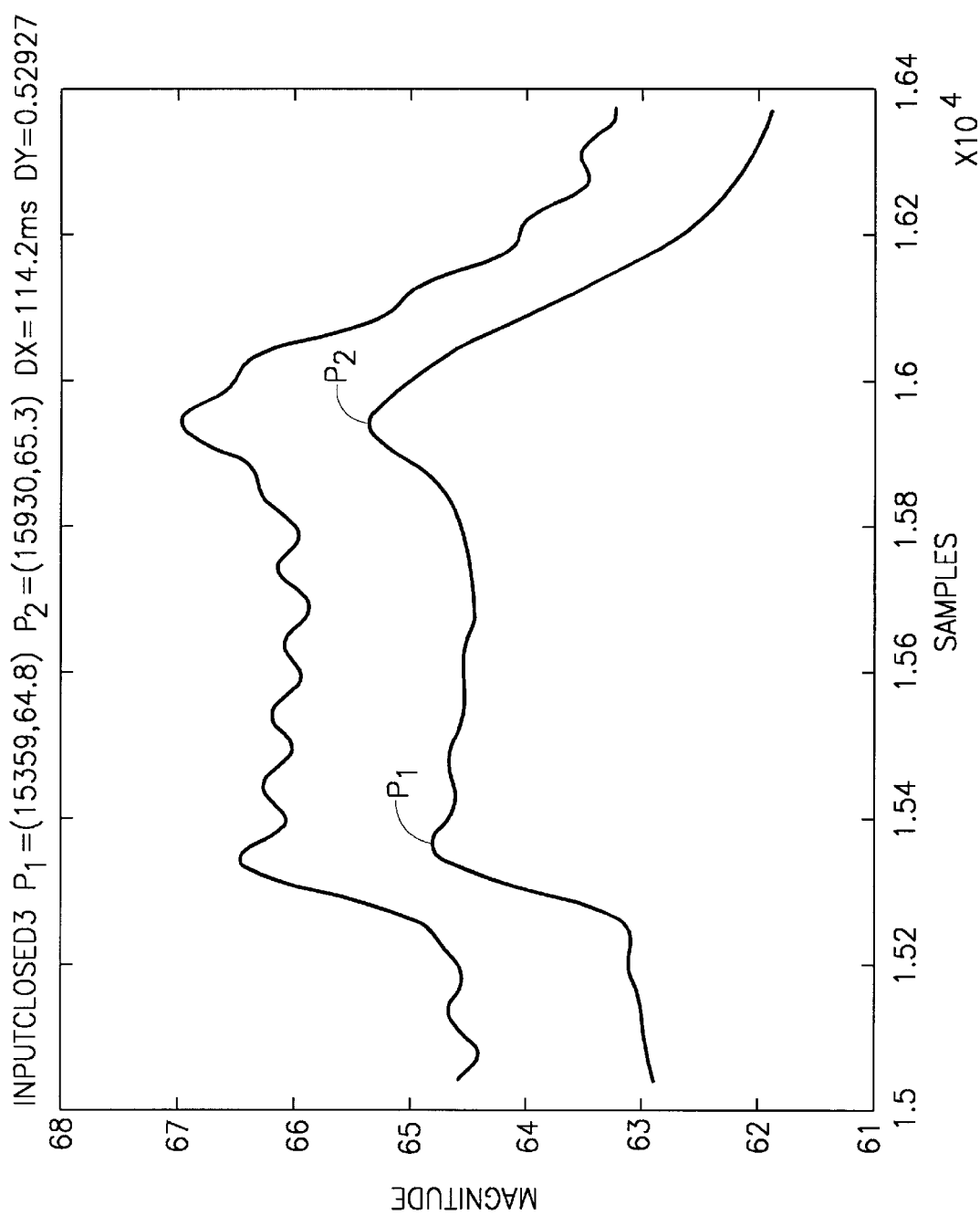
FIG. 24 is a graph of two pressure measurements, using the in-vitro system of FIGS. 5–7 and a Bio-Tek pressure calibrator as a pressure generator PSG demonstrating the forward and reflected signals.
Figure 30:
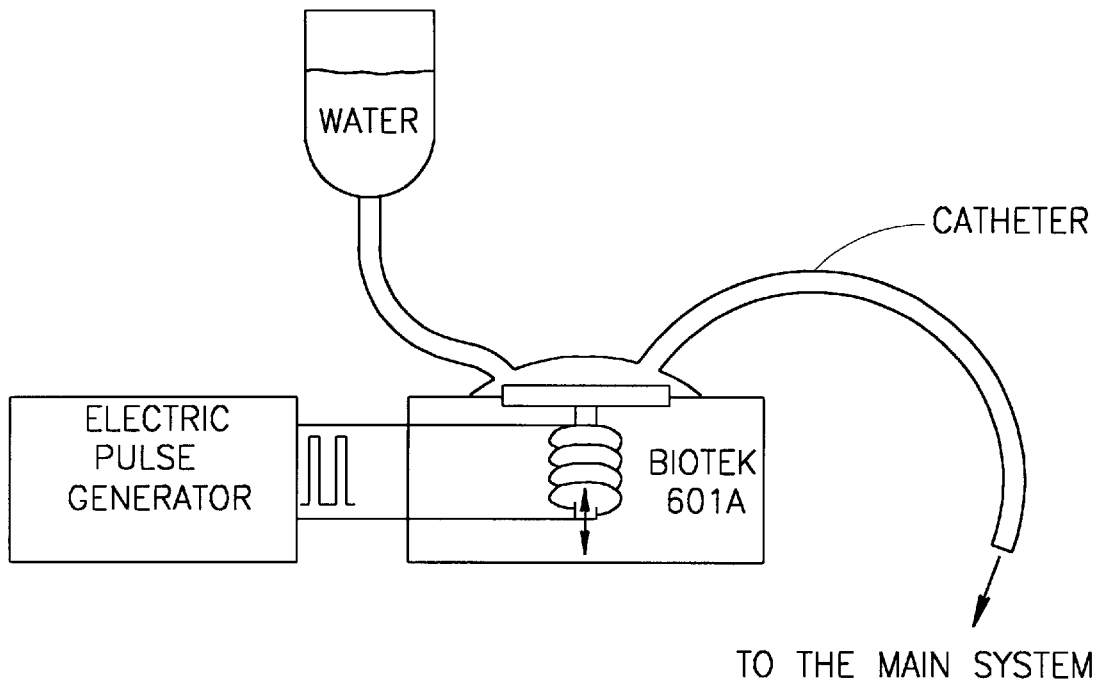
FIG. 30 schematic showing use of a Bioteck apparatus.
Figure 31:
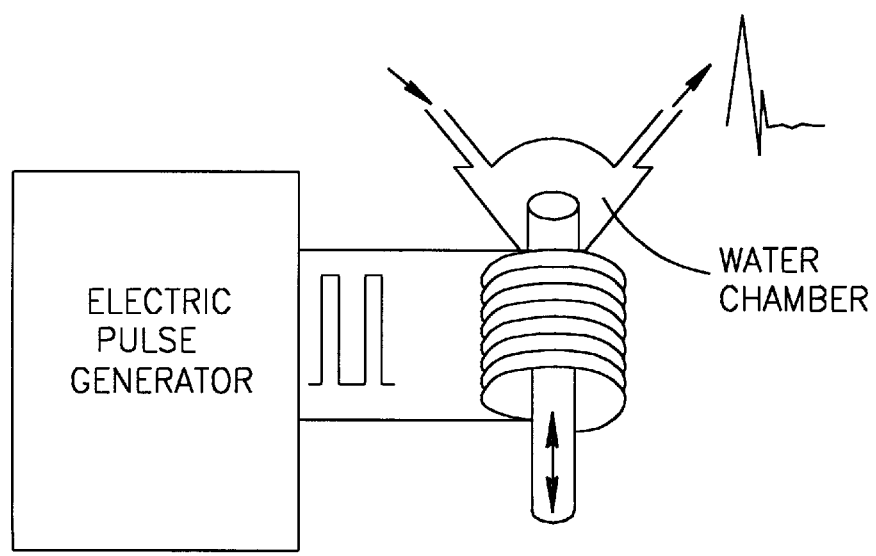
FIG. 31 is a block diagram of a PSG device having a pump with an electromagnetic push/pull mechanism.

In all the in-vitro examples given above, the PSG module was built using the presented technique of a gun pistol (FIG. 8). However, as described hereinabove, other embodiment includes the Bio-Tek, blood pressure systems calibrator Model 601A, Vermont, U.S.A. FIG. 24 presents data acquired on the in-vitro system described in FIGS. 4–7 with two pressure transducers 24a and 24b, with a pressure excitation pulse generated by the Bio-Tek calibrator, as a step function. FIG. 24 shows the step signal and the reflection from a stenosis 85 cm away. Using the derived time delay 114.2 msec, and a pressure wave velocity of 15 m/sec, the right distance is calculated. A PSG of this type is illustrated by FIGS. 29, 30 and 31 in which a pump with an electromagnetic push/pull mechanism is used to control the rapid flow of fluid needed to generate a desired pressure pulse and an external electronic pulse generator is used for excitation.

Figure 32:
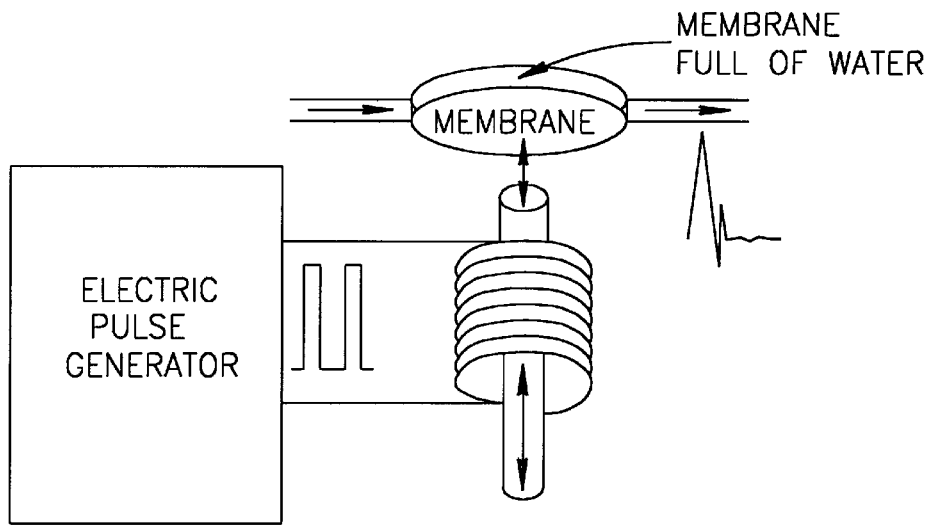
FIG. 32 is a block diagram of a PSG device having an external electromagnetic hammer operative to punch a full-of-fluid membrane.
Figure 33:
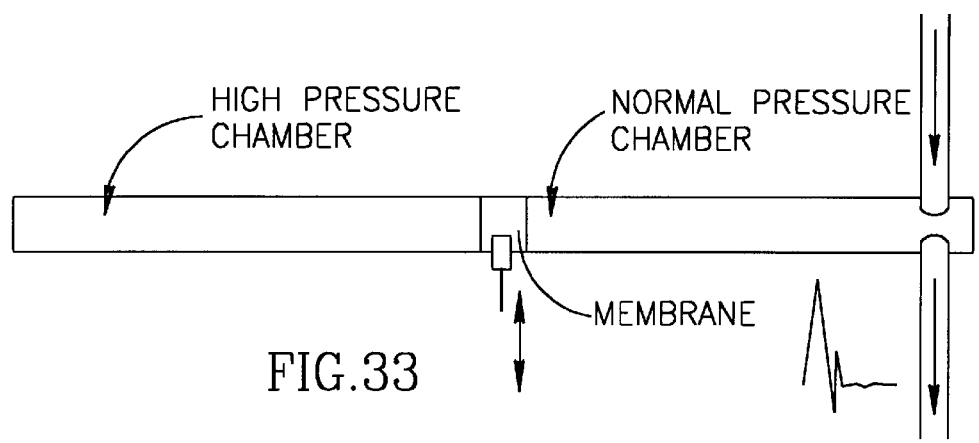
FIG. 33 is a block diagram of a PSG device having two separate membrane volumes, one with high pressure in which an external electromagnetic hammer moves or destroys a membrane separating the chambers.
Figure 34:
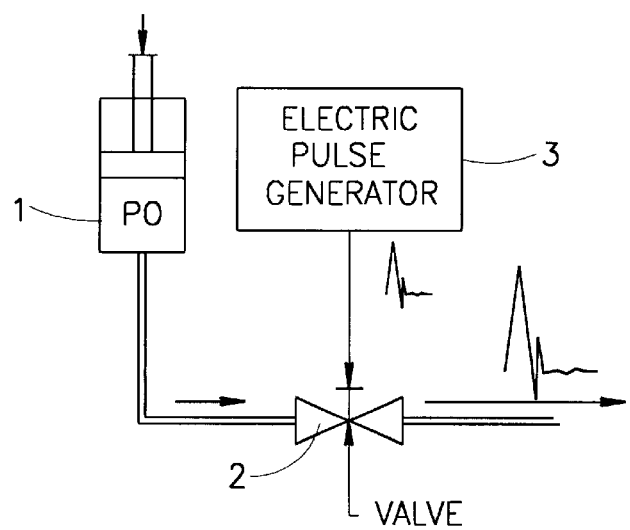
FIG. 34 is a block diagram of a PSG device having a two way linearly Proportional Flow Control Valve operated by straight DC drive signals.

Alternatively, FIG. 32 illustrates a PSG device having an external electromagnetic hammer giving a punch to a full-of-fluid membrane. The resulting punch causes a pressure pulse signal to be generated. Another PSG device is illustrated by FIG. 33 in which two separate membrane chambers having fluid volumes. One of the chambers is high pressure relative to the other. An external electromagnetic hammer moves or destroys a membrane separating the two chambers thereby generating the pressure signal. Finally, FIG. 34 illustrates a PSG device having a two ay linearly proportional flow control valve operated by straight DC drive signals. The valve when opened releases high pressure fluid that results in the generation of a pressure signal. As can be seen from these embodiments, many different variations on flow and pressure may be utilized either alone or in combination to generate the pressure signal.

It will be understood that certain features and sub-combinations are of utility and may be employed without reference to other features and sub-combinations as they are outlined within the claims. While the preferred embodiment and application of the invention has been described, it is apparent to those skilled in the art that the objects and features of the present invention are only limited as set forth in claims attached hereto.

What is claimed is:

1. An apparatus for detecting, locating and characterizing changes in a tubular conduit system within a living body for transferring fluids, said apparatus comprising:
   a signal generator configured to transmit into said tubular conduit a probe signal that changes in response to encountering changes in said tubular conduit system;
   a signal sensor operative to receive said probe signal following transmission into said tubular conduit system;
   a processor unit operatively connected to said signal sensor;
   a program for controlling the processor unit;
   said processor unit operative with said program to receive said probe signal following transmission through said tubular conduit system:
      identify changes in said probe signal;
      detect characteristics of said tubular conduit system, said characteristics of said tubular conduit system being derived from changes in said probe signal; and
      recognize and assign a value of said characteristic of said tubular conduit system.

2. The apparatus according to claim 1, wherein said processor unit is operative to select a method from a plurality of methods to identify changes in said probe signal and therefrom detect changes in said tubular conduit system.

3. The apparatus according to claim 1, wherein said tubular conduit system is a blood vessel system and said processor unit is operative to detect changes in arterial characteristics.

4. The apparatus according to claim 3 wherein said processor unit is operative to detect aneurysms.

5. The apparatus according to claim 3 wherein said processor unit is operative to detect stenosis.

6. The apparatus according to claim 3 wherein said processor unit is operative to detect arterial occlusions.

7. The apparatus according to claim 1 wherein said signal generator is a pressure signal generator.

8. The apparatus according to claim 1 wherein said signal generator is a flow signal generator.

9. The apparatus according to claim 7 wherein said signal sensor is a pressure sensor.

10. The apparatus according to claim 8 wherein said signal sensor is a pressure sensor.

11. The apparatus according to claim 7 wherein said signal sensor is a flow sensor.

12. The apparatus according to claim 7 wherein said signal sensor is adapted to measure change in a cross-sectional diameter of said tubular conduit.

13. The apparatus according to claim 7 wherein said signal sensor is an intravascular flow sensor.

14. The apparatus according to claim 7 wherein said signal sensor is an external imaging device.

15. The apparatus according to claim 3 wherein said arterial characteristics are selected from the group consisting of aneurysms, stenosis, occlusion, dissection and stent multipositioning.

16. The apparatus according to claim 8 wherein said signal sensor is a flow sensor.

17. The apparatus according to claim 8 wherein said signal sensor is adapted to measure change in a cross-sectional diameter of said tubular conduit.

18. The apparatus according to claim 8 wherein said signal sensor is an intravascular flow sensor.

19. The apparatus according to claim 8 wherein said signal sensor is an external imaging device.

20. The apparatus according to claim 3 wherein said signal generator is a pressure signal generator;
   said signal sensor is a pressure signal sensor; and
   said processor unit is operative to receive a heart beat signal; and synchronize receipt of said probe signal with said heart beat signal.

21. The apparatus according to claim 3 wherein said probe signal is a plurality of discrete signals;
   said processor unit is operative to sample said discrete signals and receive and calculate pressure wave velocity data.

22. The apparatus according to claim 21 wherein said processor unit is operative to perform a single pressure function using said discrete signals and said pressure wave velocity data.

23. The apparatus according to claim 21 wherein said processor unit is adapted to characterize the distensibility and the compliance of lesioned and non-lesioned parts of blood vessels.

24. The apparatus of claim 22 wherein said processor unit when performing said single pressure function is operative to calculate an allpass value and a cepstrum value from said minimum phase component;
   separate a regular part and a singular part of said cepstrum value, where said singular part and said regular part form said pressure wave;
   calculate an exponential function of singular part;
   evaluate a second peak time delay with respect to a forward found in said pressure signal;
   evaluate a coefficient by calculation of a second peak amplitude to determine an arterial characteristic; and
   evaluate a location and severity of said arterial characteristic.

25. The apparatus of claim 3 wherein said signal sensor includes two sensing transducers disposed in spaced apart relation.

26. The apparatus of claim 25 wherein said processor unit is operative to receive a forward pressure wave signal from a first transducer and a probe signal represented by a plurality of discrete signals sampled overtime.

27. The apparatus according to claim 26 wherein said processor unit is operative to perform a dual pressure function.

28. The apparatus of claim 27 wherein said processor unit when performing said dual pressure function is operative to:
calculate an allpass component and cepstrum component of a minimum phase component of said forward pressure wave signal received from said signal sensor;
apply an inverse filtering of said forward pressure wave signal;
apply smoothing by a B-spline function;
detect a forward peak location by a global maximum calculation;
receive a threshold value;
detect a second peak location by comparison with said threshold, where said threshold is derived from a forward peak maximum value and minimum size of a characteristic;
evaluate a second peak time delay with respect to said forward peak;
evaluate a reflection coefficient by calculating a forward and reflected peak area; and
evaluate a location and severity of said characteristic.

29. The apparatus according to claim 25 wherein said processor unit is operative to calculate a pressure wave velocity from a pressure wave sensed by said first and second transducers.

30. The apparatus according to claim 3 wherein said signal sensor is movable between at least two positions relative to said tubular conduit system and said processor unit is operative to calculate a pressure wave velocity from signals received from said two positions.

31. The apparatus according to claim 1 wherein said processor unit includes an analog to digital convertor.

32. The apparatus according to claim 1 wherein said signal sensor includes a signal conditioner.

33. The apparatus according to claim 1, wherein said tubular conduit system is a urinary vessel system and said processor unit is operative to detect changes in urinary tract characteristics.

34. The apparatus according to claim 1, wherein said processor unit is further operative to ascertain and assign a value corresponding to the location and size of said characteristic of said tubular conduit.

35. The apparatus according to claim 1, wherein said value is representative of a location of said characterized changes.

36. The apparatus according to claim 1, wherein said value is representative of a size of said characterized changes.

37. A method for using a computer to detect, locate and characterize changes in a tubular conduit system within a living body for transferring fluids wherein said computer is operatively connected to a signal generator configured to transmit into said tubular conduit a probe signal that changes in response to encountering changes in said tubular conduit system and a signal sensor operative to receive said probe signal following transmission into said tubular conduit system, said method comprising the steps of:
receiving said probe signal following transmission through said tubular conduit system:
identifying changes in said probe signal;
detecting characteristics of said tubular conduit system, said characteristics of said tubular conduit system being derived from changes in said probe signal; and
recognizing and assigning a value of said characteristic of said tubular conduit said system.

38. The method according to claim 37 including the steps of ascertaining and assigning a value corresponding to the location and size of said characteristic of said tubular conduit.

39. The method according to claim 37 further including selecting a process from a plurality of processes identifying changes in said probe signal and therefrom detecting changes in said tubular conduit system.

40. The method according to claim 37, wherein said tubular conduit system is a blood vessel system, said method further including detecting changes in arterial characteristics.

41. The method according to claim 40 including detecting aneurysms.

42. The method according to claim 40 including detecting stenosis.

43. The method according to claim 40 including detecting arterial occlusions.

44. The method according to claim 40 wherein said signal generator is a pressure signal generator, and said signal sensor is a pressure signal sensor; said method including receiving a heart beat signal; and synchronizing receipt of said probe signal with said heart beat signal.

45. The method according to claim 40 wherein said probe signal is a plurality of discrete signals; said method including sampling said discrete signals and receiving pressure wave velocity data.

46. The method according to claim 45 including the steps of performing a single pressure function using said discrete signals and said pressure wave velocity data.

47. The method of claim 46 wherein said performing step includes the step of calculating an allpass value and a cepstrum value from said minimum phase component.

48. The method of claim 46 wherein said performing step includes the step of separating a regular part and a singular part of said cepstrum value, where said singular part and said regular part form said pressure wave.

49. The method of claim 46 wherein said performing step includes the step of calculating an exponential function of singular part.

50. The method of claim 46 wherein said performing step includes the step of evaluating a second peak time delay with respect to a forward found in said pressure signal.

51. The method of claim 46 wherein said performing step includes the step of evaluating a coefficient by calculation of a second peak amplitude to determine an arterial characteristic.

52. The method of claim 46 wherein said performing step includes the step of evaluating a location of said arterial characteristic.

53. The method of claim 40 wherein said signal sensor includes two sensing transducers disposed in spaced apart relation, said method includes the step of receiving a forward pressure wave signal from a first transducer and a probe signal represented by a plurality of discrete signals sampled overtime.

54. The method according to claim 53 further including the step of calculating a pressure wave velocity from a pressure wave sensed by said first and second transducers.

55. The method according to claim 54 further including the step of performing a dual pressure function.

56. The method of claim 55 wherein said performing step includes the step of calculating an allpass component and cepstrum component of a minimum phase component of said forward pressure wave signal received from said signal sensor.

57. The method of claim 46 wherein said performing step includes the step of applying an inverse filtering of said forward pressure wave signal.

58. The method of claim 56 wherein said performing step includes the step of applying smoothing by a B-spline function.

59. The method of claim 56 wherein said performing step includes the step of detecting a forward peak location by a global maximum calculation.

60. The method of claim 56 wherein said performing step includes the step of receiving a threshold value.

61. The method of claim 56 wherein said performing step includes the step of detecting a second peak location by comparison with said threshold, where said threshold is derived from a forward peak maximum value and minimum size of a characteristic.

62. The method of claim 56 wherein said performing step includes the step of evaluating a second peak time delay with respect to said forward peak.

63. The method of claim 56 wherein said performing step includes the step of evaluating a reflection coefficient by calculating a forward and reflected peak area.

64. The method of claim 56 wherein said performing step includes the step of evaluating a location of said characteristic.

65. The method of claim 56 wherein said performing step includes the step of calculating a pressure wave velocity from a pressure wave sensed by said first and second transducers.

66. The method according to claim 39 wherein said signal sensor is movable between at least two positions relative to said tubular conduit system, said method including the step of calculating a pressure wave velocity from signals received from said two positions.

67. The method according to claim 40 wherein said signal sensor is a flow sensor.

68. The method according to claim 40 wherein said signal sensor is adapted to measure change in a cross-sectional diameter of said tubular conduit.

69. The method according to claim 40 wherein said signal sensor is an intravascular flow sensor.

70. The method according to claim 40 wherein said signal sensor is an external imaging device.

71. The method according to claim 40 wherein said arterial characteristics are selected from the group consisting of aneurysms, stenosis, occlusion, dissection and stent multipositioning.

* * * * *